(12) United States Patent
Rinck et al.

(10) Patent No.: US 11,501,460 B2
(45) Date of Patent: Nov. 15, 2022

(54) MAGNETIC RESONANCE IMAGING SYSTEM AND METHOD

(71) Applicant: Siemens Healthcare GmbH, Erlangen (DE)

(72) Inventors: Daniel Rinck, Forchheim (DE); David Grodzki, Erlangen (DE); Rene Kartmann, Nuremberg (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/103,258

(22) Filed: Nov. 24, 2020

(65) Prior Publication Data

US 2021/0158563 A1 May 27, 2021

Related U.S. Application Data

(60) Provisional application No. 62/941,326, filed on Nov. 27, 2019.

(51) Int. Cl.
*G06T 7/70* (2017.01)
*G01R 33/28* (2006.01)
*G01R 33/56* (2006.01)

(52) U.S. Cl.
CPC .......... *G06T 7/70* (2017.01); *G01R 33/283* (2013.01); *G01R 33/5608* (2013.01); *G06T 2207/10088* (2013.01); *G06T 2207/30036* (2013.01); *G06T 2207/30041* (2013.01)

(58) Field of Classification Search
CPC ............ G06T 7/70; G06T 2207/10088; G06T 2207/30036; G06T 2207/30041; G01R 33/283; G01R 33/5608
See application file for complete search history.

(56) References Cited

U.S. PATENT DOCUMENTS

| 4,875,485 A | * | 10/1989 | Matsutani | ............... | G01R 33/28 600/415 |
| 5,296,811 A | * | 3/1994 | Ehnholm | ............ | G01R 33/383 324/318 |
| 6,011,396 A | * | 1/2000 | Eckels | ............... | G01R 33/3806 324/300 |
| 2009/0093706 A1 | | 4/2009 | Zhang et al. | | |
| 2012/0153953 A1 | * | 6/2012 | Grodzki | ............. | G01R 33/3806 324/318 |
| 2012/0220855 A1 | | 8/2012 | Zhang et al. | | |

(Continued)

OTHER PUBLICATIONS

European Search Report for Application No. 20206846.6 dated Apr. 20, 2021.

*Primary Examiner* — G. M. A Hyder

(57) ABSTRACT

In a method for performing a magnetic resonance measurement of an organ structure of a patient using a magnetic resonance imaging system adapted to the imaging of the organ structure: a correct positioning of the organ structure of the patient is ascertained, a correct positioning of the magnetic resonance imaging system with regard to the positioning of the organ structure of the patient is ascertained, a magnetic resonance scanning protocol is selected, a spatial coverage of the magnetic resonance measurement with regard to the organ structure to be imaged is adjusted, and the magnetic resonance measurement is performed to acquire magnetic resonance image data of the organ structure.

20 Claims, 5 Drawing Sheets

(56) References Cited

U.S. PATENT DOCUMENTS

Figure 1:
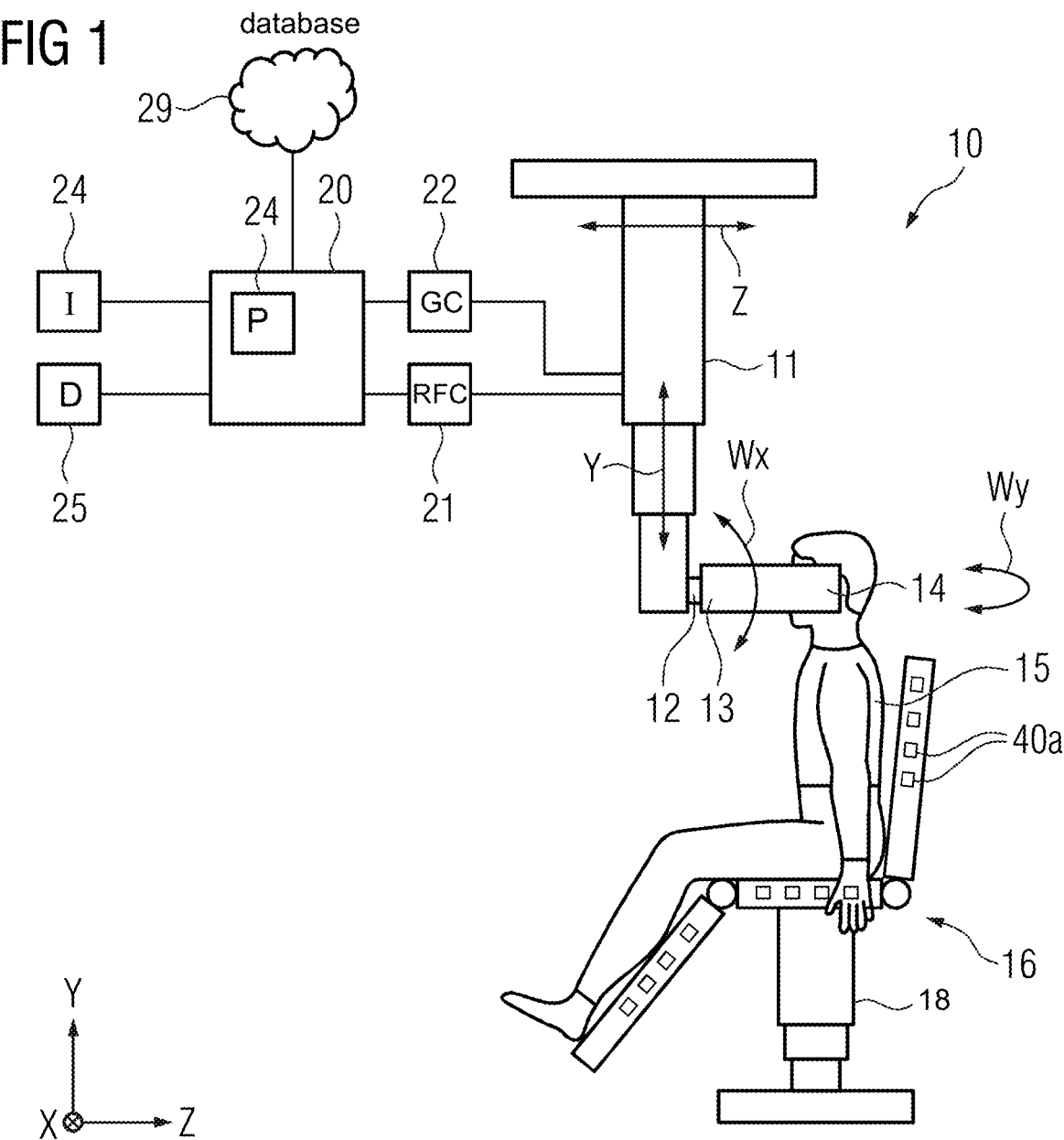

| | | |
|---|---|---|
| 2013/0223704 A1 | 8/2013 | Lay et al. |
| 2013/0279779 A1 | 10/2013 | Darrow et al. |
| 2014/0155736 A1 | 6/2014 | Vaidya et al. |
| 2015/0323618 A1* | 11/2015 | Merfeld ............ G01R 33/3875 324/321 |
| 2021/0156938 A1* | 5/2021 | Greiser ............ G01R 33/3802 |

* cited by examiner

MAGNETIC RESONANCE IMAGING SYSTEM AND METHOD

CROSS REFERENCE TO RELATED APPLICATIONS

This patent application claims priority to, and the benefit of, U.S. Provisional Patent Application No. 62/941,326, filed Nov. 27, 2019, which is incorporated herein by reference in its entirety.

BACKGROUND

Field

The disclosure relates to a method for performing a magnetic resonance measurement of an organ structure of a patient using a magnetic resonance imaging system particularly adapted to the imaging of the organ structure, a magnetic resonance imaging system, comprising a processor and a computer program product that can be loaded into a memory of a programmable processor of a magnetic resonance imaging system.

Related Art

For examination of diseases of different body parts and organs a wide variety of dedicated diagnostic modalities is employed. Often, those diagnostic modalities provide limited spatial resolution of the body parts in question and/or utilize ionizing radiation to acquire two-dimensional or three-dimensional images of the body parts. For example, diseases of the teeth and the periodontium, such as caries or periodontitis, are typically diagnosed with X-ray-based imaging methods. For this purpose, conventional or digital X-ray projection methods, and recently also three-dimensional (3D) X-ray imaging methods, are used. In another example, imaging of the eyes is usually performed with dedicated cameras restricted to providing a front-view image of the eye. There exist numerous other diagnostically modalities dedicated to specific body parts or organ structures of a patient, many of which comprise at least one of the limitations described above.

A major disadvantage of X-ray-based imaging methods is constituted by the need for exposing a patient to ionizing radiation. Magnetic resonance tomography is an imaging method that avoids using ionizing radiation. Furthermore, magnetic resonance tomography typically provides an enhanced soft tissue contrast in comparison to X-ray-based imaging methods and natively supports three-dimensional imaging of an examination object. Thus, magnetic resonance tomography represents a potential alternative to known dedicated diagnostic modalities for diagnostic imaging of specific body parts.

Magnetic resonance tomography represents a prominent imaging method for acquiring images of an interior of the examination object. In order to carry out a magnetic resonance measurement, the examination object is positioned in a strong and homogeneous, static magnetic field (B0 field) of a magnetic resonance imaging system. The static magnetic field may comprise magnetic field strengths of 0.2 Tesla to 7 Tesla in order to align nuclear spins within the examination object with the static magnetic field. For triggering so-called nuclear spin resonances, radiofrequency excitation pulses are emitted into the examination subject. Each radiofrequency excitation pulse causes a magnetization of nuclear spins within the examination object to deviate from the static magnetic field by an amount which is known as the flip angle. A radiofrequency excitation pulse may be provided via a high frequency magnetic field alternating with a frequency which corresponds to the Larmor frequency at the respective static magnetic field strength. Excited nuclear spins may exhibit a rotating and decaying magnetization (magnetic resonance signal), which can be detected using dedicated radiofrequency antennas. For spatial encoding of measured data, rapidly switched magnetic gradient fields are superimposed on the static magnetic field.

The received nuclear magnetic resonances are typically digitized and stored as complex values in a k-space matrix. This k-space matrix provides a basis for a reconstruction of magnetic resonance images and for determining spectroscopic data. A magnetic resonance image is typically reconstructed by means of a multi-dimensional Fourier transformation of the k-space matrix.

In avoiding ionizing radiation, magnetic resonance tomography is particularly suitable for continuous or repetitious diagnostic monitoring, for example within the framework of a longitudinal imaging study. Longitudinal imaging studies may comprise carrying out a plurality of imaging examinations to determine a progression of a disease or a success of a therapeutic treatment over an elongated period of time. Disadvantages usually associated with magnetic resonance tomography are:

- a high expenditure of time required for performing the magnetic resonance measurement in comparison to other imaging methods,
- a high level of complexity related to preparing and performing a magnetic resonance measurement as well as
- a requirement of expert knowledge for interpreting the results of the magnetic resonance measurement.

These workflow-related aspects pose a challenge for a broad application of magnetic resonance imaging as a diagnostic modality for imaging of specific body parts or organs structures of a patient.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 a schematic representation of a magnetic resonance imaging system according to an exemplary embodiment the disclosure.

Figure 2:
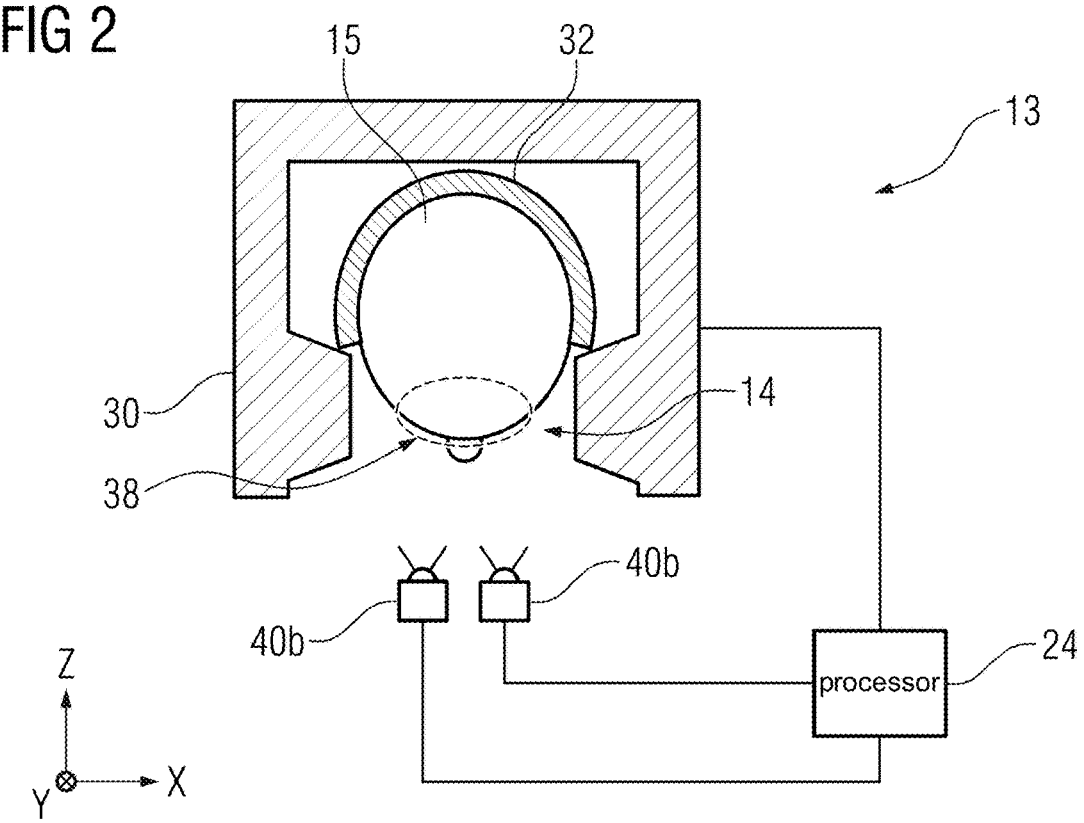

FIG. 2 a schematic representation of a magnetic resonance imaging system according to an exemplary embodiment the disclosure.

Figure 3:
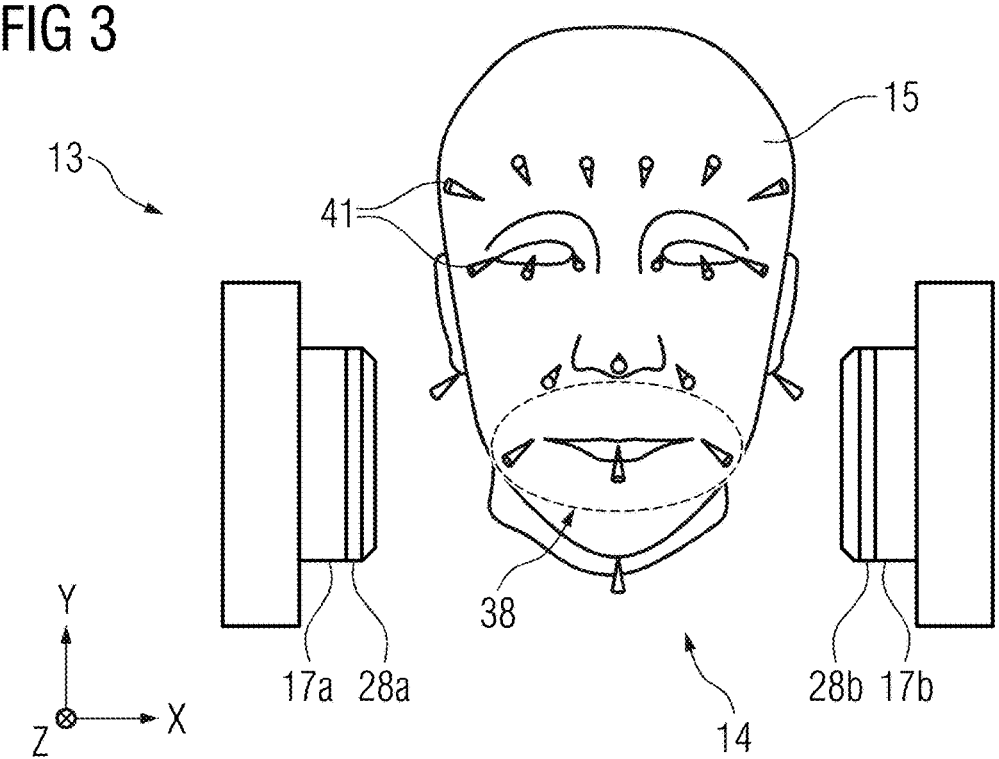

FIG. 3 a schematic representation of a magnetic resonance imaging system according to an exemplary embodiment the disclosure.

Figure 4:
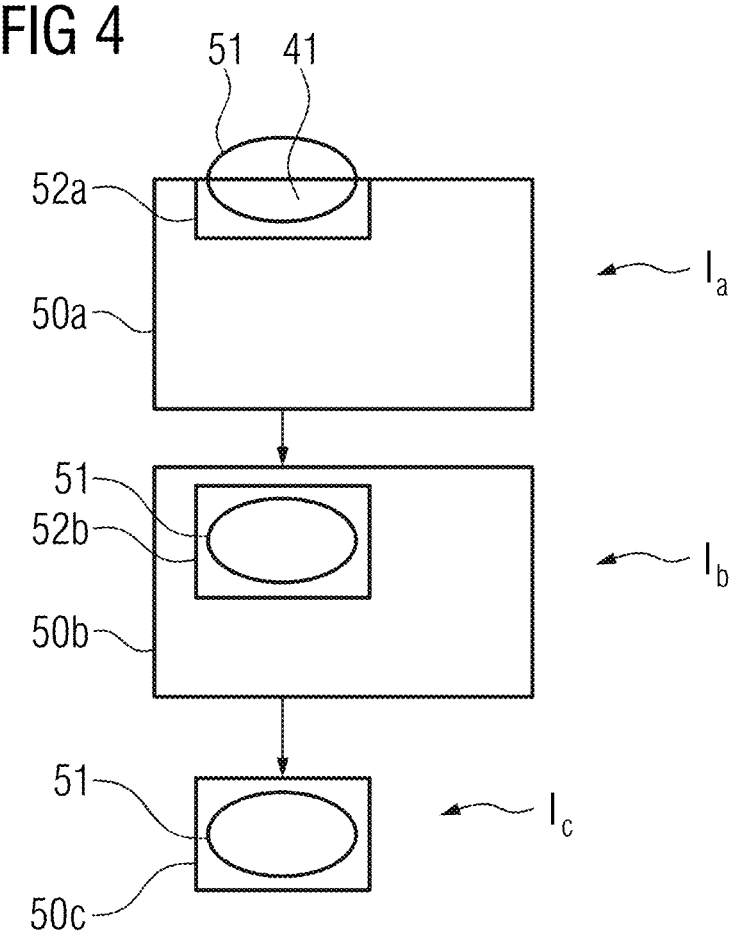

FIG. 4 a flowchart of a method for iteratively adjusting a field of view of a magnetic resonance measurement according to an exemplary embodiment the disclosure.

Figure 5:
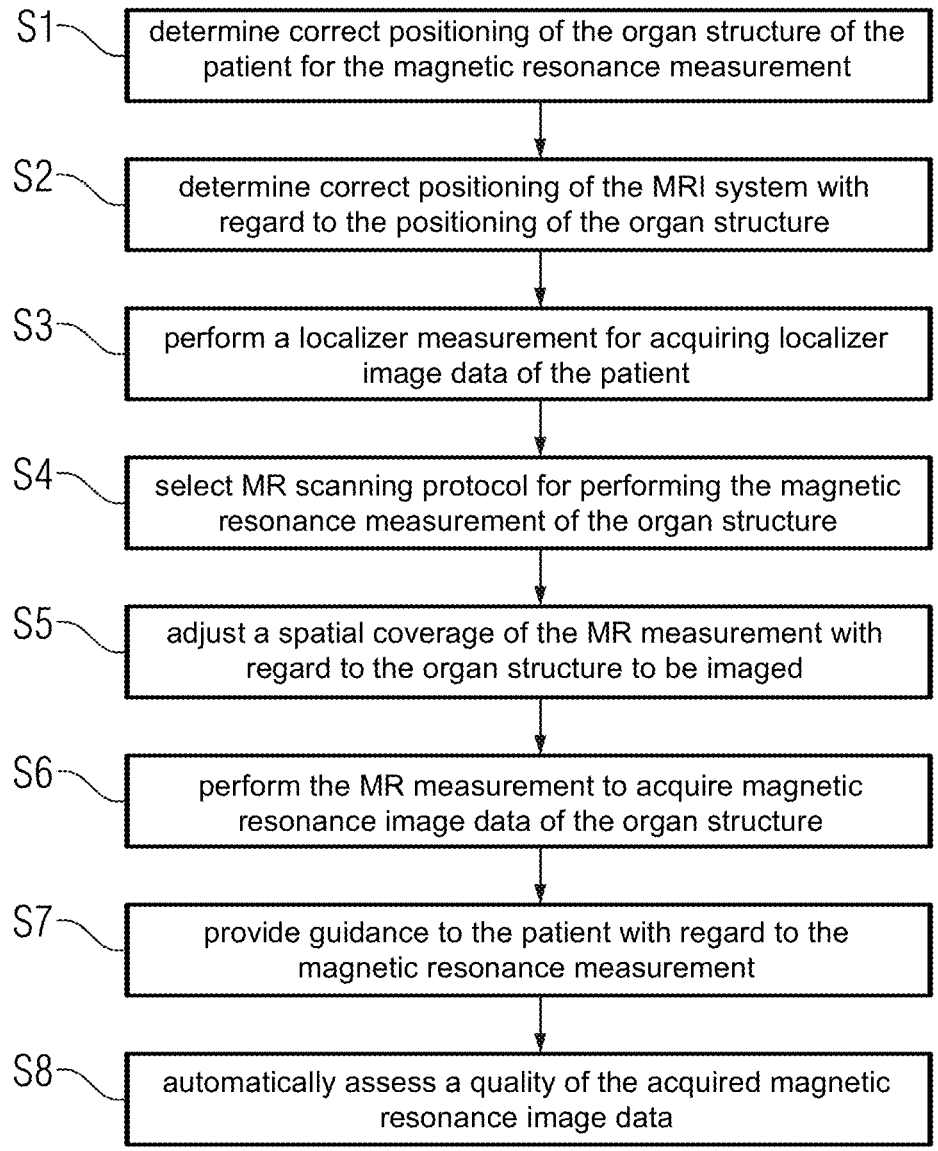

FIG. 5 a flowchart of a method for performing a magnetic resonance measurement of an organ structure according to an exemplary embodiment the disclosure.

Figure 6:
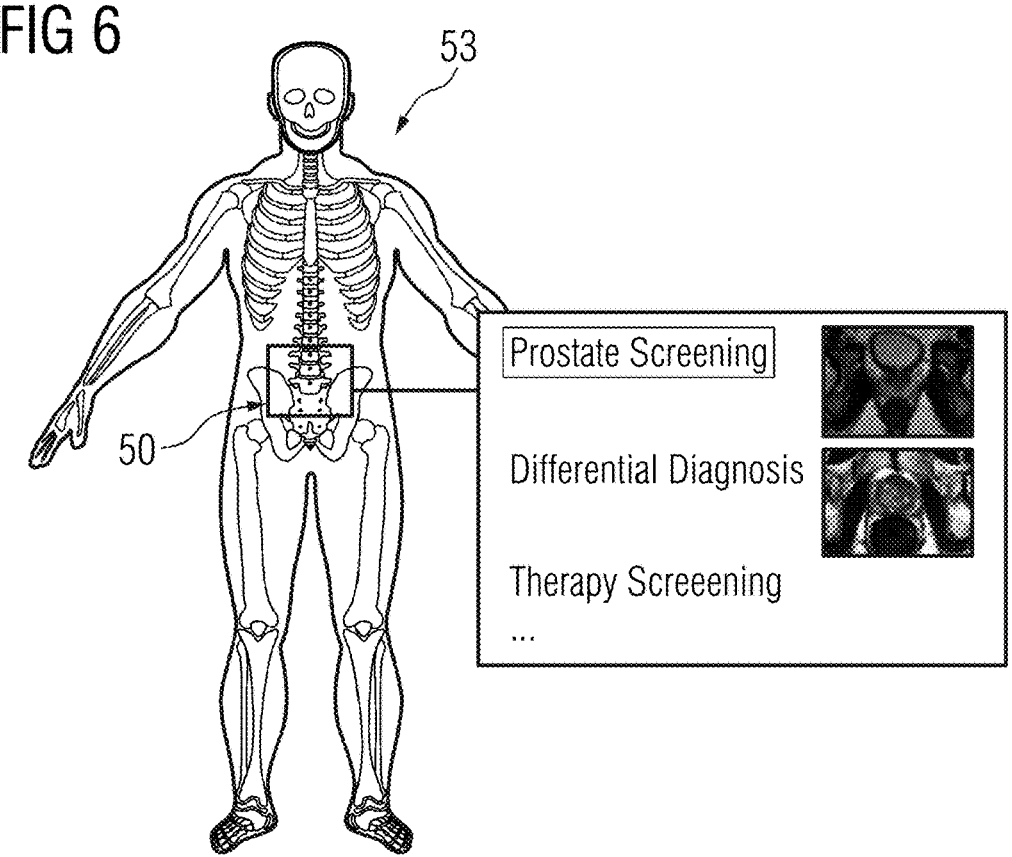

FIG. 6 an example graphical representation of a patient according to an exemplary embodiment the disclosure.

Figure 7:
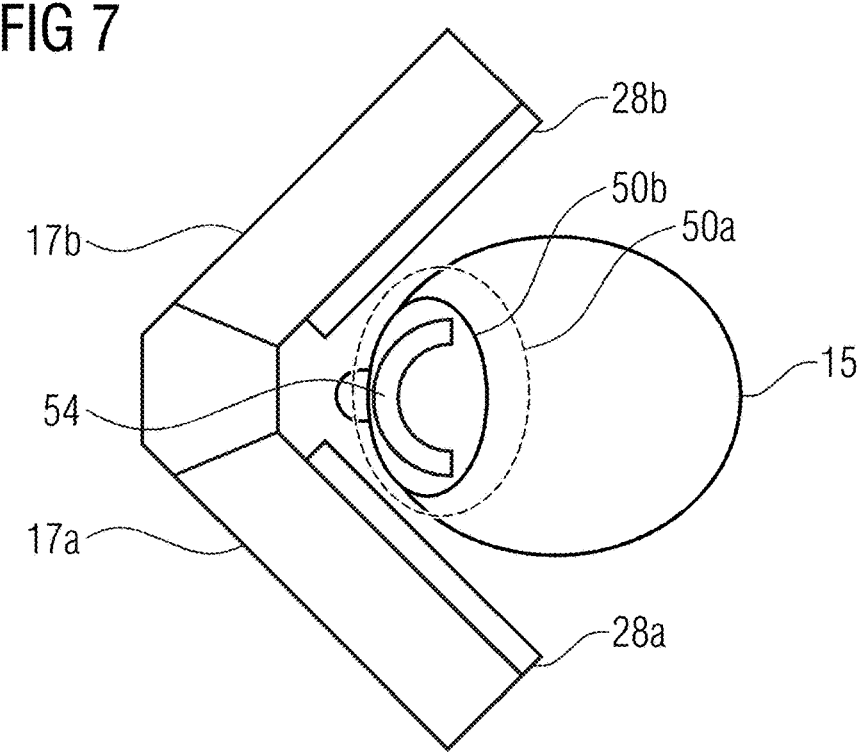

FIG. 7 a magnetic resonance imaging system according to an exemplary embodiment the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to improve the workflow of a magnetic resonance measurement of a dedicated body part or organ structure of a patient.

This object is achieved by a method, a magnetic resonance imaging system and a computer program product according to the disclosure.

According to a method of an exemplary embodiment, a magnetic resonance measurement of an organ structure of a patient is performed using a magnetic resonance imaging system particularly adapted to the imaging of the organ structure, comprising the steps:
- ascertaining a correct positioning of the organ structure of the patient for the magnetic resonance measurement,
- ascertaining a correct positioning of the magnetic resonance imaging system with regard to the positioning of the organ structure of the patient,
- selecting a magnetic resonance scanning protocol for performing the magnetic resonance measurement of the organ structure,
- adjusting a spatial coverage of the magnetic resonance measurement with regard to the organ structure to be imaged and
- performing the magnetic resonance measurement to acquire magnetic resonance image data of the organ structure.

For preparation of the magnetic resonance measurement, the patient may be positioned in an imaging region of the magnetic resonance imaging system configured to perform a magnetic resonance measurement of the organ structure of the patient. An imaging region may represent a volume wherein the patient is positioned for performing the magnetic resonance measurement of the patient. The imaging region may be at least partially encompassed by a magnetic field generator of the magnetic resonance imaging system. For example, the imaging region may be confined by the magnetic field generator in at least one spatial direction, at least two spatial directions or at least three spatial directions. It is also conceivable, that the imaging region is encompassed by the magnetic field generator in a circumferential direction.

The magnetic field generator may be configured to provide a homogenous, static magnetic field (B0-field), a magnetic gradient field and/or a high frequency magnetic field (B1-field) in the imaging region of the magnetic resonance imaging system. In an exemplary embodiment, the magnetic field generator is configured to provide an imaging volume within the imaging region, the imaging volume being characterized by a particularly homogenous magnetic field or an approximately linear magnetic gradient field. The imaging volume may be an isocenter of the magnetic resonance imaging system. In a conceivable embodiment, a dimension of the imaging volume approximately corresponds to a dimension of the organ structure to be imaged. For providing a static magnetic field, the magnetic field generator may comprise a magnet or a magnet arrangement including a plurality of magnets. A magnet may be a permanent magnet, an electromagnet, a superconducting magnet and/or a high-temperature superconducting magnet.

The magnetic field generator may further comprise a high frequency system and/or a magnetic gradient field system. The high frequency system may be configured to generate the high frequency magnetic field in the imaging region of the magnetic resonance imaging system. In an exemplary embodiment, the high frequency system comprises at least one radiofrequency antenna configured for emitting a radiofrequency excitation pulse into the patient and/or receiving magnetic resonance signals from the organ structure of the patient.

It is conceivable, that the magnetic resonance imaging system at least partially encloses a part of the patient, such as a head, a leg, an arm, an abdomen or the like, when the patient is positioned in the imaging region. Particularly, the part of the patient at least partially enclosed by the magnetic resonance imaging system may comprise the organ structure to be imaged. The organ structure may comprise an organ, such as a heart, a brain, an eye, a prostate, a breast, but also soft and/or hard tissue, such as skin, bone, dentin, enamel, periorbital tissue and the like. Of course, other organ structures and tissues as the ones mentioned here are also conceivable.

In one step of the inventive method, a correct positioning of the organ structure of the patient is ascertained for the magnetic resonance measurement.

A correct positioning of the organ structure for the magnetic resonance measurement may be accomplished when the organ structure of the patient is positioned within the imaging region, particularly the imaging volume, of the magnetic resonance imaging system. The correct positioning may be characterized by a desirable predefined relative position between the organ structure and the magnetic resonance imaging system, particularly the imaging volume of the magnetic resonance imaging system. Ascertaining the correct positioning of the organ structure may comprise supporting and/or guiding the patient to take a desired position and/or posture in such a way, that the organ structure is located in a desired position. However, ascertaining the correct positioning of the organ structure may also comprise employing methods or techniques which ensure that the organ structure remains in the desired position throughout the magnetic resonance measurement and/or the preparation of the magnetic resonance measurement. In another example, ascertaining the correct positioning of the organ structure may comprise supporting the patient to sustain a specific position and/or posture, which is beneficial for imaging of the organ structure.

In particular, the magnetic resonance imaging system may comprise a sensor, e.g. a two-dimensional (2D) camera and/or a 3D camera, for acquiring a sensor signal indicative of a current position and/or posture of the patient. Based on the current position and/or posture of the patient, a difference to a desired position and/or posture of the patient may be determined. The desired position and/or posture of the patient may depend on the organ structure to be imaged. It is conceivable, that the desired position and/or posture of the patient is determined during preparation of the magnetic resonance measurement and/or obtained from a reference database.

Ascertaining the correct positioning of the organ structure may further comprise outputting a feedback regarding the difference between the current position and/or posture of the patient and the desired position and/or posture of the patient. For example, the feedback may be output to the patient and/or the operator via a suitable output unit. The output unit may be a projector unit configured to project the desired position and/or posture of the patient onto a patient supporting device, such as a patient chair, a patient couch or a patient table. However, the output unit may also comprise a display and/or a speaker configured to inform the patient and/or the operator visually and/or audibly on a required adjustment to the position and/or posture of the patient. In an exemplary embodiment, the difference between the current position and/or posture of the patient and the desired position and/or posture of the patient is used for automatically adjusting the position of the patient. For this purpose, the patient supporting device may comprise motor elements configured to adjust a position and/or an orientation of the patient with respect to the magnetic resonance imaging device.

In a further embodiment, ascertaining the correct positioning of the organ structure may involve the patient to operate adjustment means and/or the positioning system of the magnetic resonance imaging system. For example, the patient may be visually and/or audibly instructed to adjust his position and/or posture to match the organ structure with the imaging volume. This is particularly advantageous, as the patient can judge best, if the position and/or posture is comfortable enough to endure a duration of the magnetic resonance measurement.

According to one step of the inventive method, a correct positioning of the magnetic resonance imaging system with regard to the positioning of the organ structure of the patient is ascertained.

The magnetic resonance imaging system may be a dedicated scanner comprising adjustment means such as a pivot mounted arm, a lever and/or a supporting element for supporting and/or adjusting a position of the patient and/or a specific body part of the patient. It is also conceivable, that the dedicated scanner is at least partially mounted on a positioning system, such as a rail system, a pivot arm and/or a telescope system, in such a way, that the dedicated scanner may be positioned in a desired relative position to the patient. The positioning of the dedicated scanner relative to the patient may comprise positioning the imaging volume relative to the organ structure of the patient.

The magnetic resonance imaging system may further include a patient supporting device. The patient supporting device may comprise adjustment means which may be adjusted and/or moved to support the patient and/or a body part of the patient in a desirable position. The patient supporting device may comprise adjustable cushions to increase comfort of the patient in any position and/or posture required for the magnetic resonance measurement.

In an exemplary embodiment, ascertaining the correct positioning of the magnetic resonance imaging system may comprise matching a position of the imaging volume the organ structure of the patient via adjustment of the positioning system and/or the adjustment means of the magnetic resonance imaging system. A relative position between the magnetic resonance imaging system and the patient may be determined via a sensor, such as a 2D camera, a 3D camera, an ultrasound sensor, a distance sensor and/or other suitable sensors. Analogous to the step described above, a difference between a current relative position between the magnetic resonance imaging system and the patient and a desired relative position between the magnetic resonance imaging system and the patient may be determined in dependence of a sensor signal acquired via the sensor. In an exemplary embodiment, ascertaining the correct positioning of the magnetic resonance imaging system with regard to the patient comprises determining a required adjustment of a position and/or orientation of the magnetic resonance imaging system in dependence of the difference. The required adjustment of the position and/or orientation of the magnetic resonance imaging system may subsequently be output to the patient, the operator and/or a motor element configured for controlling the position and/or orientation of the magnetic resonance imaging system.

It is conceivable, that an imaging parameter of the magnetic resonance measurement, such as a field of view and/or a spatial coverage, is readjusted in dependence of the position and/or posture of the patient during the magnetic resonance measurement. However, the position and/or orientation of the magnetic resonance imaging system and/or components of the magnetic resonance imaging system may also be adjusted to compensate for a movement of the patient and/or track different organ structures of the patient during the magnetic resonance measurement. Thus, magnetic resonance image data of a plurality of organ structures may favorably be acquired during the magnetic resonance measurement.

In one step of the inventive method, a magnetic resonance scanning protocol for performing the magnetic resonance measurement of the organ structure is selected.

The magnetic resonance scanning protocol may comprise, for example, a pulse sequence and/or an imaging parameter of the magnetic resonance measurement. In an exemplary embodiment, the selection of the magnetic resonance scanning protocol is performed automatically. In one embodiment, the selection of the scanning protocol may be carried out in dependence of a scanning prescription of the patient and/or a referral of a physician. The scanning prescription may comprise information on the magnetic resonance measurement to be performed as well as the organ structure in question and/or an indication of the patient. It is also conceivable, that the scanning prescription comprises information on a target body region of the patient as well as an imaging parameter, a dimension of a field of view, a resolution and/or a desired contrast setting of the magnetic resonance measurement. The scanning prescription may also indicate a specific type of magnetic resonance measurement. For example, the scanning prescription may indicate the magnetic resonance measurement to be a screening scan, such as a projection measurement or a localizer measurement. Such a screening scan may provide a time-effective solution for determining a general status of an eye or a tooth of the patient. A projection measurement may represent a magnetic resonance measurement, without spatial encoding in one spatial direction. Thus, a 2D projection image of a 3D imaging volume within the patient may be obtained. However, the scanning prescription may also indicate that a detailed examination of the organ structure of the patient is to be performed, for instance for determining an inflammatory state of a tooth of the patient. For this purpose, 3D magnetic resonance image data from the tooth of the patient may be acquired. For this purpose, the selection of the magnetic resonance scanning protocol may comprise adjusting the field of view of the magnetic resonance measurement to match the tooth of the patient.

However, it is also conceivable to manually select the magnetic resonance scanning protocol based on a pre-selection of magnetic resonance scanning protocols provided by the magnetic resonance imaging system. The magnetic resonance imaging system may determine one or more potentially fitting magnetic resonance scanning protocols in dependence of the scanning prescription, the referral and/or the requested body region of the patient. The pre-selection of magnetic resonance protocols may be presented to the operator for selection. In confirming at least one of the presented magnetic resonance scanning protocols, the magnetic resonance measurement may be initiated. In an exemplary embodiment, the pre-selection of magnetic resonance scanning protocols is displayed to the operator in conjunction with a graphical representation, such as a patient avatar and/or a pre-view of images/orientation. For example, the representation may be obtained from a body model of the patient and/or from a reference database. In providing an inventive method for selecting the magnetic resonance scanning protocol, a magnetic resonance measurement can favorably be carried out by medical personnel with limited experience in radiology, such as dentists, cardiologists and/or ophthalmologists.

According to one embodiment, the selection of the magnetic resonance scanning protocol may be carried out in dependence of a localizer measurement (scout). The localizer measurement may be performed with preliminary imaging parameters adapted to the size of the organ structure. The preliminary imaging parameters may be selected manually or automatically. It is also conceivable, that a default setting of preliminary imaging parameters is provided in dependence of the organ structure to be imaged, the scanning prescription and/or the referral. However, preliminary imaging parameters dependent on the organ structure may also be selected manually or derived in dependence of optical image data provided via an optical sensor and/or a body model of the patient. The magnetic resonance scanning protocol may be selected in dependence of the position of the organ structure within localizer image data acquired via the localizer measurement. In an exemplary embodiment, if the localizer measurement reveals a possible existence of a pathology of the organ structure of the patient, a detailed magnetic resonance measurement of the respective organ structure may be initiated. The existence of a pathology may be detected, for example, by an image processing algorithm, an expert system, a neural network, a method of deep learning and/or other types of intelligent algorithms.

In one step of the inventive method, a spatial coverage of the magnetic resonance measurement is adjusted with regard to the organ structure to be imaged.

A spatial coverage of the magnetic resonance measurement may be characterized by a dimension of the imaging volume, a dimension of the organ structure to be imaged and/or a position of the imaging volume with respect to the patient. Particularly, the spatial coverage may indicate a relative position between the imaging volume and the organ structure to be imaged. A desirable spatial coverage may be achieved, when a diagnostically relevant part of the organ structure is completely enclosed within the imaging volume. In an exemplary embodiment, a share or volume of tissue and/or other matter irrelevant to a diagnosis of the organ structure in the imaging volume is reduced. However, the spatial coverage may also relate to the spatial resolution of the organ structure to be imaged. Thus, adjusting the spatial resolution may have an impact on a quality of the magnetic resonance image data and/or a time required to perform the magnetic resonance measurement.

In one embodiment, the spatial coverage of the magnetic resonance measurement may be determined in dependence of optical image data of the patient acquired via a camera and/or other optical sensor. Using an optical sensor may be particularly convenient if the body region of the patient containing the organ structure to be imaged is easily accessible with optical imaging. For example, an easily accessible body region may be the head region of the patient, particularly the eye region, the jaw region and/or the teeth region. The camera and/or optical sensor may track facial landmarks of the patient, such as an eye, an eyebrow, a nose, a lip, a chin, a mouth, a cheekbone and the like. The spatial coverage may be determined based on an absolute position and/or a relative position of facial landmarks tracked via the optical sensor. It is conceivable that adjusting the spatial coverage may be further supported by using a body model of the patient. The body model may be derived in dependence of the optical image data and/or the tracked landmarks of the patient. In particular, the body model may comprise information on an approximate location of the organ structure to be imaged.

In a further embodiment, landmarks may be provided by magnetic resonance visible markers positioned within the patient or on a surface of the patient. For dental imaging it is particularly useful to position the magnetic resonance visible marker or a plurality of magnetic resonance visible markers in an oral cavity of the patient when preparing the magnetic resonance measurement. The magnetic resonance visible marker may comprise a capsule containing vitamin D, vitamin E or cod liver oil, which may be placed inside the oral cavity of the patient. However, one or more magnetic resonance visible markers may also be attached to a mouthguard or a brace positioned in an intraoral cavity of the patient. In a further example, one or more magnetic resonance visible markers may be attached to a supporting element of the magnetic resonance imaging system configured to stabilize movement of the head of the patient. In an exemplary embodiment, the magnetic resonance visible markers are detected via a screening scan, such as a localizer measurement and/or a projection measurement. As described above, an absolute position and/or relative position of the magnetic resonance visible markers may be derived from image data acquired via the screening scan. Adjusting the spatial coverage may subsequently be carried out in dependence of an absolute position and/or a relative position of magnetic resonance visible markers.

In still a further embodiment, the spatial coverage is determined in dependence of landmarks provided by a contrast agent enriched in the organ structure to be imaged and/or an organ structure located in proximity to the organ structure to be imaged. For this purpose, a contrast agent may be injected into the patient during preparation of the magnetic resonance measurement. The contrast agent may be any contrast agent known in the state of the art. Particularly, for imaging of the prostate, the contrast agent may also be water or a mixture of water and contrast agent deposited in the bladder of the patient. Thus, the bladder may easily be detected in image data acquired from a screening scan, and a position of the bladder may be determined. A position of the prostate may subsequently be determined in dependence of the determined position of the bladder. It is conceivable, that a body model providing information on a typical and/or statistical localization of the prostate in relation to the bladder is used for determining the position of the prostate. For imaging of the teeth region and/or the jaw region, a contrast agent may be pasted and/or greased on the teeth of the patient during preparation of the magnetic resonance measurement. For this purpose, a dedicated paste or grease may be used, which provides a suitable magnetic resonance contrast. In an exemplary embodiment, the paste or grease contains biocompatible and non-toxic substances. However, the paste or grease may also comprise commercial contrast agents in permissible quantities. For imaging of other organ structures, contrast agents may be applied in a typical manner. In conceivable embodiments, contrast media may be detected within ventricles and/or blood vessels. Thus, easily detectable landmarks may be provided, particularly for cardiac imaging, neurological imaging and/or brain imaging.

In one step of the inventive method, the magnetic resonance measurement is performed to acquire magnetic resonance image data of the organ structure.

The magnetic resonance measurement may be started automatically once requirements of the preceding steps have been fulfilled. In particular, the correct positioning of the organ structure and the correct positioning of the magnetic resonance imaging system must have been ascertained, the magnetic resonance scanning protocol must have been selected and the spatial coverage of the magnetic resonance measurement with regard to the organ structure must have been adjusted. It is conceivable, that an initiation of the magnetic resonance measurement is dependent on a manual input of the operator and/or the patient.

In one embodiment, actions related to one or more of the previously described steps are continued throughout the magnetic resonance measurement. For example, the correct positioning of the organ structure and the correct positioning of the magnetic resonance imaging system may be ascertained throughout the magnetic resonance measurement. It is also conceivable, that the spatial coverage is continuously adjusted with regard to the organ structure when performing the magnetic resonance measurement. For this purpose, the organ structure of the patient may be tracked during the magnetic resonance measurement.

In providing a method according to the disclosure, the magnetic resonance imaging system may favorably be operated by less experienced personnel with regard to magnetic resonance imaging. Thus, smaller and/or specialized clinics focusing for example on orthopedics, ophthalmology and/or dentistry may favorably benefit from enhanced diagnostic imaging capabilities, such as high soft tissue contrast and/or 3D imaging. Furthermore, via at least a partial automatization of the preparation and/or execution of the magnetic resonance measurement, a number of required operator interactions may be reduced and a time-efficiency of magnetic resonance examination, including preparation of the patient, may be increased.

In one embodiment of the inventive method, ascertaining the correct positioning of the organ structure may comprise locking or fixing at least a body part of the patient in a predefined relative position with regard to the magnetic resonance imaging system.

The magnetic resonance imaging system may comprise one or more adjustable mechanical elements and/or fasteners configured to fix at least a body part of the patient in a predefined relative position with regard to the magnetic resonance imaging system. Thus, the organ structure may be prevented from leaving the desired position and/or posture during the magnetic resonance measurement.

In an example particularly suitable for dental imaging, the magnetic resonance system may comprise a mouthguard for the patient to bite upon during the magnetic resonance measurement. The mouthguard may be positioned in the intraoral cavity of the patient during preparation of the magnetic resonance measurement. It is conceivable, that the mouthguard comprises a sensor, such as a pressure sensor and/or an optical sensor, providing a sensor signal indicative of a correct positioning of the mouthguard within the patient's mouth. Thus, the correct positioning of the teeth and/or a jaw of the patient may be monitored. However, the mouthguard may also limit a movement of the teeth region, the jaw region and/or the head of the patient, in order to prevent the organ structure to be imaged from leaving the desired position. In one embodiment, the mouthguard is attached to a supporting structure outside the intraoral cavity of the patient, thus limiting movement of the head of the patient during the magnetic resonance measurement.

In locking or fixing at least a body part of the patient in a predefined relative position to the magnetic resonance imaging system, a movement of the patient during the magnetic resonance measurement can favorably be reduced or avoided. Thus, an occurrence of image artifacts related to deliberate motion of the patient during the magnetic resonance measurement can advantageously be diminished.

According to an embodiment of the inventive method, ascertaining the correct positioning of the magnetic resonance imaging system with regard to the positioning of the organ structure of the patient comprises adjusting a position of at least one part of a magnetic field generator of the magnetic resonance imaging system.

In order to ascertain the correct positioning of the magnetic resonance imaging system, an orientation and/or a position of the magnetic resonance imaging system may be adjusted via the positioning system and/or the adjustment means. Particularly, individual components of the magnetic field generator, such as a magnet, a radiofrequency antenna and/or a gradient coil, may be adjusted in order to ascertain the correct positioning of the magnetic resonance imaging system with regard to the positioning of the organ structure. For example, the orientation and/or the position of individual components may be adjusted with respect to each other, with respect to the examination room and/or with respect to the patient. In one example, the high frequency system may comprise a radiofrequency emitting antenna and a radiofrequency receiving antenna, which may be positioned independently from one another, from a magnet and/or from a gradient coil. However, individual components may also be adjusted collectively with other components.

In providing means for adjusting the position of the at least one part of the magnetic field generator, less technologically sophisticated dedicated scanners can be used for magnetic resonance imaging. Thus, cost and space requirement can be favorably reduced with regard to conventional magnetic resonance imaging systems.

In an exemplary embodiment of the inventive method, ascertaining of the correct positioning of the magnetic resonance imaging system with regard to the positioning of the organ structure of the patient comprises
    acquiring a sensor signal indicative of a current relative position between the organ structure and at least one reference point of the magnetic resonance imaging system and determining a required modification to the positioning of the magnetic resonance imaging system in dependence of the sensor signal indicative of the current relative position between the organ structure and the at least one reference point of the magnetic resonance imaging system, wherein the position of the at least one part of the magnetic field generator is adjusted in dependence of the required modification.

The adjustment of the position of the magnetic resonance imaging system may be carried out in dependence of a sensor signal indicative of a current relative positioning between the organ structure and the at least one reference point of the magnetic resonance imaging system. For this purpose, one or more sensors, such as a pressure sensor, an optical sensor, an ultrasound sensor, a photo sensor, a thermal sensor, a position sensor and the like, may be employed. For example, a sensor signal may comprise optical image data of the patient and the magnetic resonance imaging device, pressure data indicating a pressure distribution exerted by the patient on a component of the magnetic resonance imaging device, a heat signature of the patient in proximity to the imaging region of the magnetic resonance imaging device and/or positional information of the patient related to an orientation of the patient with respect to a force of gravity.

However, other sensor signals and/or sensor data are also conceivable. At least one sensor may be configured to track a movement of the patient and/or a movement of a body part of the patient relative to the reference point of the magnetic resonance imaging system. For this purpose, in an exemplary embodiment, an optical sensor, such as a 3D camera and/or a 2D camera is used. For tracking a movement of the patient, a temporal progression of the sensor signal may be analyzed, from which a movement of the patient may be derived and/or quantified. Particularly, a temporal progression of a position and/or posture of the patient may be determined based on the acquired sensor signal.

For determining a relative position between the organ structure to be imaged and the position and/or posture of the patient, a body model of the patient may be used. The body model may comprise information related to a location of the organ structure with respect to a posture of the patient. Thus, a current relative position between the organ structure and the at least one reference point of the magnetic resonance imaging may be determined in dependence of the current patient position and/or posture of the patient, the body model as well as the current relative position between the patient and the at least one reference point of the magnetic resonance imaging system. For determining the required modification to the positioning of the magnetic resonance imaging system, a difference between the current relative position between the organ structure and the at least one reference point and a desired relative position between the organ structure and the at least one reference point may be derived. The desired relative position between the organ structure and the at least one reference point may be obtained from a reference database.

The reference point may be an arbitrarily chosen point on a surface of the magnetic resonance imaging system. However, the reference point may also be a geometric or volumetric center of the magnetic resonance imaging system. In other conceivable embodiments, the reference point may be a colored and/or reflective marker on a surface of the magnetic resonance imaging system, which may be detected via the one or more sensors. In an exemplary embodiment, the reference point is the center of the imaging volume. The center of the imaging volume may be known to the magnetic resonance imaging system in every possible configuration and/or arrangement of the magnetic resonance imaging system, the positioning system and/or the adjustment means. In one embodiment, the position of the imaging volume is adjusted in dependence of the movement of the sensor signal indicative of the current relative position between the organ structure and the at least one reference point of the magnetic resonance imaging system.

Information on a required adjustment of the magnetic resonance imaging system or a component therefore may be output to the operator and/or the patient. Thus, the operator and/or the patient may carry out the required adjustment manually in dependence of the information. For example, the operator and/or the patient may be visually and/or audibly instructed to adjust the position of the at least one part of the magnetic field generator to match the organ structure with the imaging volume. This is particularly advantageous, as the patient can judge best, if the position and/or posture is comfortable enough to endure a duration of the magnetic resonance measurement.

However, the position of the at least one part of the magnetic field generator may also be adjusted automatically or semi-automatically, e.g. after a confirmation via the operator and/or the patient. For an automatic adjustment, the magnetic resonance imaging system and/or components of the magnetic resonance imaging system may comprise motor elements which may be controlled in dependence of the required modification to the positioning of the magnetic resonance imaging system. It is also conceivable, that the sensor signal is used to determine and/or predict a collision of a component of the magnetic resonance imaging system with the patient. Such a collision may be avoided by automatically clearing an estimated movement trajectory of the patient via the positioning system and/or the adjustment means.

Ascertaining the correct positioning of the magnetic resonance imaging system may comprise manually or automatically adjusting the position and/or orientation of the magnetic resonance imaging system and/or a component of the magnetic resonance imaging system. In particular, a position and/or orientation of the at least one part of the magnetic field generator may automatically be adjusted in dependence of the required modification.

In determining the required modification to the positioning of the magnetic resonance imaging system in dependence of the sensor signal and the reference point, ascertaining the correct positioning of the magnetic resonance imaging device can be carried out in a robust and reproducible manner. Thus, image artifacts related to patient movement during the magnetic resonance measurement can favorably be reduced or avoided.

According to a further embodiment of the inventive method, the ascertaining of the correct positioning of the magnetic resonance imaging system with regard to the positioning of the organ structure of the patient comprises acquiring an information indicative of a physical characteristic of the patient and/or an imaging situation and determining a required modification to the positioning of the magnetic resonance imaging system in dependence of the physical characteristic of the patient and/or the imaging situation, wherein the position of the at least one part of the magnetic field generator is adjusted in dependence of the required modification.

The magnetic resonance system may comprise sensors for acquiring information indicative of a physical characteristic of the patient, such as a weight, a dimension and/or an electrical property of the patient (e.g. an electrical conductivity). In particular, information indicative of a physical characteristic of the patient may be derived from a sensor signal. It is also conceivable, that the physical characteristic comprises a posture of the patient, which may be determined in dependence of a suitable sensor signal as described above. In one embodiment, physical properties of the patient may be obtained from a medical prescription, a referral, and/or a medical database.

Information indicative of a physical characteristic of the patient may be used for deriving a body model. The body model may comprise information on specific features of the patient, such as a fat content, a water content, but also further information, such as a location of an organ structure and/or a dimension of the patient, a body part and/or an organ structure. In one embodiment, the body model of the patient may be used to determine a desired relative position between the patient and the magnetic resonance imaging system. However, the desired relative position between the patient and the magnetic resonance imaging system may also be obtained from the prescription, from the imaging situation and/or a reference database.

The imaging situation may comprise, for example, screening or imaging of a specific organ structure in context of differential diagnosis, therapy, intervention and the like. In particular, the imaging situation may relate to a specific body region and/or organ structure. For example, the imaging situation may relate to cardiac imaging, mammography imaging, neurological imaging, urological imaging, orthopedics imaging, ophthalmological imaging or dental imaging. According to the imaging situation, different requirements related to an accuracy of the correct positioning of the magnetic resonance imaging system and/or an available time allocation for the magnetic resonance measurement may need to be fulfilled. As an example, the imaging situation may be obtained from the scanning prescription of the patient. The imaging situation may also specify the desired relative position between the patient and the magnetic resonance imaging system and/or components of the magnetic resonance imaging system.

In an exemplary embodiment, the required modification to the positioning of the magnetic resonance imaging system is determined in dependence of the desired relative position between the patient and the magnetic resonance imaging system and the information indicative of a physical characteristic of the patient. Ascertaining the correct positioning of the magnetic resonance imaging system may comprise manually or automatically adjusting the position and/or orientation of the magnetic resonance imaging system and/or a component of the magnetic resonance imaging system in dependence of the required modification. In particular, a position and/or orientation of the at least one part of the magnetic field generator may automatically be adjusted in dependence of the required modification.

By ascertaining the correct positioning of the magnetic resonance imaging system in dependence of a posture and/or a physical characteristic of the patient as well as an imaging situation, the magnetic resonance measurement can favorably be adapted to individual boundary conditions. For example, the magnetic resonance measurement may be sped up in emergency situations or the relative position between the magnetic resonance imaging system and the patient may be adapted to take into account an obesity of the patient.

According to one embodiment of the inventive method, the ascertaining of the correct positioning of the magnetic resonance imaging system with regard to the positioning of the organ structure of the patient comprises
performing a localizer measurement for acquiring localizer image data of the patient and
detecting a landmark within the localizer image data, wherein the landmark is a tooth and/or an eye of the patient,
wherein the position of the at least one part of the magnetic field generator is adjusted in dependence of the detected landmark.

A localizer measurement may be a projection measurement or a navigator measurement. Detecting a tooth and/or an eye of the patient as a landmark within the localizer measurement as well as determining a position of the organ structure to be imaged in dependence of the landmark may be carried out according to an embodiment described below. However, in one embodiment, the tooth and/or the eye of the patient may represent the organ structure to be imaged. In this case, the position of the at least one part of the magnetic field generator may be adjusted directly in dependence of a position of the landmark detected within the localizer image data.

In detecting a tooth and/or an eye of the patient as landmarks in a localizer measurement, the position and or an orientation of the head of the patient can favorably be determined with high accuracy.

In a further embodiment of the inventive method, the organ structure is at least one tooth or at least one eye of the patient, wherein the ascertaining of the correct positioning of the magnetic resonance imaging system with regard to the positioning of the organ structure of the patient comprises
acquiring optical image data of the at least one eye and/or a jaw region comprising the at least one tooth via an optical sensor,
wherein the position of the at least one part of the magnetic field generator is adjusted in dependence of the acquired optical image data.

In an exemplary embodiment, a 3D camera and/or a 2D camera is used to acquire optical image data of the at least one eye and/or a jaw region comprising the at least one tooth. The acquisition of optical image data may comprise acquiring optical image data of a facial region of the patient. However, it is also conceivable, that the acquisition of optical image data is limited to an eye and/or the jaw region of the patient. Acquiring optical image data of the at least one eye and/or a jaw region comprising the at least one tooth may also be carried out to an embodiment described below.

In acquiring optical image data of the organ structure to be imaged, a spatial location of the organ structure can be determined in a time-efficient and reliable manner. Thus, a duration for ascertaining the correct positioning of the magnetic resonance imaging system with regard to the positioning of the organ structure of the patient can favorably be reduced.

In an embodiment of the inventive method, a sensor signal indicative of a position and/or posture of the patient is acquired, wherein the adjusting of the spatial coverage of the magnetic resonance measurement with regard to the organ structure to be imaged comprises an iterative adjustment of a field of view of the magnetic resonance measurement in dependence of a body model of the patient and the sensor signal indicative of the position and/or posture of the patient.

In a first iteration, an estimated field of view may be determined in dependence of the body model of the patient. For this purpose, the body model may comprise a plurality of body landmarks and/or organ boxes, which may be learned or trained in dependence of image data for various patient postures. The image data may be acquired, for example, from magnetic resonance measurements but also from a reference database comprising image data acquired with different imaging modalities. For instance, an organ box may indicate a rough position of a specific organ structure for a specific posture of the patient. When performing a magnetic resonance measurement of the specific organ structure of the patient positioned in the specific posture, the position of the specific organ structure may be detected and the position of the organ box in the body model may be refined. Thus, with an increasing number of magnetic resonance measurements, an accuracy of a positioning of the organ box representing the specific organ structure may be enhanced.

In an exemplary embodiment, a 3D camera and/or a plurality of 2D cameras are used to acquire optical image data of the patient. The optical image data may be used to determine the current position and/or posture of the patient. Subsequently, a positioning of the organ structure to be imaged may be determined in dependence of the current position and/or posture of the patient and the position of the organ box of the respective organ structure provided via the body model. Thus, in the first iteration, the field of view may be estimated in dependence of the body model and optical image data acquired via a camera. In order to evaluate the estimated field of view, a first localizer measurement may be performed to acquire first localizer image data of the organ structure. If the field of view is undesirable, a second iteration may be performed. For example, the field of view may be undesirable, if the organ structure to be imaged is not entirely covered by the field of view.

For the second iteration, a second field of view may be determined in dependence of a position of the organ structure to be imaged within the first localizer image data. Subsequently, a second localizer measurement may be carried out to validate the position of the organ structure within the second localizer image data. If the field of view is still undesirable, a third or fourth iteration may be carried out accordingly. However, the second field view determined in dependence of the first localizer image data may already provide a desirable field of view for performing the magnetic resonance measurement.

In an example particularly suitable for prostate imaging, the magnetic resonance imaging system may comprise a plurality of pressure sensors mounted within the patient supporting device. The patient supporting device may comprise an approximately triangular shape or a saddle shape configured to accommodate the patient in a sitting position. The sensor signal provided by the pressure sensors may comprise a spatially resolved pressure distribution exerted by the patient on the patient supporting device. The sensor signal may be used to determine the position and/or the posture of the patient on the patient supporting device. In a further embodiment, the sensor signal indicative of the position and/or posture of the patient may also be acquired via at least one of an optical sensor, a distance sensor, a position sensor of a radiofrequency receiving antenna and/or a thermal sensor. A distance sensor may be any kind of sensor configured to determine a distance between the patient and the magnetic resonance imaging system, particularly a reference point on the patient and a reference point on the magnetic resonance imaging system. For example, the distance sensor may comprise a capacitive, an electromagnetic (e.g. radar, ultrasound), an optical and/or an inductive measurement principle. In an exemplary embodiment, the distance sensor is more efficient in the task of determining the distance between the patient and the magnetic resonance imaging system as compared to a camera. A thermal may comprise a contacting or a contactless measurement principle. In an exemplary embodiment, the thermal sensor may be a thermographic camera. The thermographic camera may determine a heat signature of the patient, which may be used to determine the position and/or the posture of the patient. A position sensor may also be understood as an inclinometer or a tilt sensor. The position sensor may be configured to determine a position and/or an orientation of a reference object, such as the patient and/or the radiofrequency receiving antenna. The position sensor may also comprise a gyroscope and an accelerometer to determine an angle of the reference object with respect to a force gravity. It is conceivable, that at least two sensors with different measurement principles are used to determine the position and/or posture of the patient. For example, a distance sensor and a position sensor may be used to determine the position and/or posture of the patient. In an exemplary embodiment, the position sensor is configured to determine the orientation of a radiofrequency receiving antenna positioned in proximity to the patient. However, further combinations of the sensors mentioned above are also conceivable.

It is conceivable, that a body model of the patient is estimated in dependence of the sensor signal. The body model may comprise geometric information on a specific body region of the patient or the whole body of the patient. In particular, the body model may comprise information on a location of the organ structure to be imaged within the body of the patient. In one embodiment, the body model is used for an iterative adjustment of the field of view of the magnetic resonance measurement. However, the body model may also be used for an iterative optimization of the position and/or the posture of the patient.

In a further embodiment, the magnetic resonance imaging system comprises a camera, such as a 2D camera, a 3D camera, an infrared camera, a thermal imaging camera and the like, configured to acquire optical image data of the patient. In dependence of the optical image data, machine-learning methods and/or other forms of artificial intelligence may be employed to determine landmarks of the patient, such as an absolute position and/or a relative arrangement of ears, eyes, eyebrows, a nose, a mouth, a cheekbone, but also extremities, such as arms and/or legs. In one example, optical image data from the head of the patient may be acquired from multiple different camera angles. Based on the determined landmarks on the patient's head, an individual body model may be provided that can be used for determining a current position and/or posture of the patient. Furthermore, the individual body model of the patient may be supplemented with statistical information on a location of the organ structure to be imaged based on image data and/or organ localization probabilities obtained from a reference database. The adjusting of the spatial coverage of the magnetic resonance measurement may comprise an iterative adjustment of a field of view of the magnetic resonance measurement in dependence of the individual body model.

In automatically adjusting the field of view of the magnetic resonance measurement in dependence of a sensor signal indicative of the position and/or posture of the patient, the magnetic resonance measurement can advantageously compensate for a movement of the patient. Thus, image artifacts due to motion of the patient can favorably be reduced or avoided.

In a further embodiment, the inventive method comprises the step of performing a localizer measurement for acquiring localizer image data of the patient, wherein a landmark is detected in the localizer image data, wherein the landmark is a tooth and/or an eye of the patient and wherein the adjusting of the spatial coverage of the magnetic resonance measurement with regard to the organ structure to be imaged is carried out in dependence of the landmark in the localizer image data.

A localizer measurement may comprise a time-efficient magnetic resonance measurement to acquire localizer image data of the patient and/or a body region of the patient. The localizer measurement may comprise limitations regarding a quality, a spatial resolution and/or an image resolution of acquired localizer image data. However, the localizer image data may provide sufficient spatial resolution for detecting anatomical features, such as body parts or organs, of the patient.

In one embodiment, a localizer measurement may be carried out to acquire localizer image data of the body region containing the organ structure to be imaged. The localizer image data may be analyzed to detect landmarks of the patient. In an exemplary embodiment, the localizer measurement may be a projection measurement. However, it is also conceivable that a navigator measurement and/or a regular magnetic resonance measurement is performed in order to detect landmarks within the patient. For example, for imaging of the teeth of the patient, one tooth or a plurality of teeth may provide landmarks which may be detected in the magnetic resonance image data, particularly the projection image data. It is conceivable, that the spatial coverage of the magnetic resonance measurement is adjusted in dependence of a position of the teeth within the projection image data. However, an absence of a specific tooth or a plurality of specific teeth may also provide for landmarks to be detected. An information on the absence of specific teeth may be obtained from an information system used by the operator of the magnetic resonance imaging system, as for example a dentist. In order to detect a tooth of the patient as a landmark, the imaging parameters of the localizer measurement may be specifically adapted to provide high or low contrast of teeth.

Similarly, an eye of the patient may provide a landmark which may be detected in the localizer image data. In order to detect the eye of the patient as a landmark, in an exemplary embodiment, imaging parameters of the localizer measurement are adapted to provide high contrast of soft tissue of the patient. In an embodiment, both a tooth and an eye of the patient are detected as landmarks via a single localizer measurement. In an exemplary embodiment, the imaging parameters of such a localizer measurement are adapted to provide a high contrast of soft tissue. Conversely, a contrast of the tooth would usually be dark, as there would be minimal magnetic resonance signal expected from the enamel and/or the dentin of the tooth. However, a lack of a magnetic resonance signal may also provide a landmark to be detected.

As described above, the detected landmarks may be used to determine a position and/or posture of the patient as well as a position of the organ structure to be imaged and the spatial coverage of the magnetic resonance measurement may be adjusted accordingly in an automatic, semi-automatic or manual manner.

In detecting a tooth and/or an eye of the patient as a landmark via a localizer measurement, the position of the organ structure to be imaged can reliably be determined with low computational effort. This is particularly advantageous, as a complexity of a workflow can be decreased and an accuracy of determining the current position of the organ structure can be increased.

In an exemplary embodiment, the inventive method comprises the further step:

performing (S3) a localizer measurement for acquiring localizer image data of the patient, wherein the organ structure is segmented in the localizer image data and wherein the spatial coverage of the magnetic resonance measurement is automatically adjusted (S5) in dependence of a position of the organ structure within the localizer image data if the organ structure is completely captured within the localizer image data or wherein a subsequent localizer measurement for acquiring subsequent localizer image data is performed if at least a part of the organ structure is positioned outside of the localizer image data and wherein the spatial coverage of the magnetic resonance measurement is automatically adjusted (S5) in dependence of a position of the organ structure within the subsequent localizer image data.

According to an embodiment described above, an estimated position of the organ structure to be imaged may be determined in dependence of a body model of the patient and a sensor signal indicative of a position and/or posture of the patient. However, it is also conceivable, that the position of the organ structure is determined via a localizer measurement comprising a comparably high spatial coverage of the body of the patient. Thus, a high probability of capturing at least a part of the organ structure to be imaged within the localizer image data may be provided. Similar to an embodiment described above, the organ structure may be detected in the localizer image data via landmarks. The detection of landmarks may be supported via application of a neural network and/or a deep learning algorithm trained for detection of specific landmarks, such as a tooth, an eye, a bone, an enamel, a dentin, a prostate or any other organ or tissue within the patient. In an exemplary embodiment, landmarks are chosen which are positioned in proximity to the organ structure to be imaged. However, the landmark may also represent the organ structure or be a part of the organ structure to be imaged.

After detection of the organ structure within the localizer image data, a segmentation of the organ structure may be performed. The organ structure may be roughly segmented in such a way, that an examination of the spatial coverage of the organ structure is still possible. Examining the spatial coverage may comprise checking if the organ structure is entirely captured within the localizer image data. If the organ structure is not fully captured in the localizer image data and/or if the organ structure could not be segmented completely, a subsequent localizer measurement may be performed in order to refine the spatial coverage. For example, the field of view of the subsequent localizer measurement may be increased and/or shifted to better cover the organ structure. However, adjusting the spatial coverage may also comprise adjusting a volume of surrounding tissue covered by the magnetic resonance measurement and/or a spatial resolution of the organ structure. For example, in adjusting the field of view to reduce a coverage of diagnostically irrelevant tissue, the spatial resolution of the organ structure may be increased without increasing the time required for performing the magnetic resonance measurement. If the spatial coverage of the subsequent localizer measurement is still undesirable, further localizer measurements may be carried out accordingly. However, the spatial coverage determined in dependence of the subsequent localizer measurement may already provide a desirable spatial coverage for performing the magnetic resonance measurement.

In automatically adjusting the spatial coverage in dependence of a localizer measurement, a desirable spatial coverage can be obtained with less computational effort compared to embodiments using a body model of the patient. Thus, computational capabilities and costs of the magnetic resonance imaging system can favorably be decreased.

According to a further embodiment of the inventive method, the organ structure is at least one tooth or at least one eye of the patient, wherein optical image data of the at least one eye and/or a jaw region comprising the at least one tooth is acquired via an optical sensor and wherein the spatial coverage of the magnetic resonance measurement with regard to the at least one tooth or the at least one eye is automatically adjusted (S5) in dependence of the optical image data.

For acquiring optical image data from the at least one tooth or the at least one eye, an accessibility to a facial region of the patient may be exploited. The accessibility to the facial region of the patient may be provided via a physical access, such as an entry, a clearance and/or an unobstructed view, which may be used to acquire optical image data of the at least one eye and/or a jaw region comprising the at least one tooth via at least one optical sensor. The accessibility may further comprise a clearance for a mechanical element, such as a fixation element and/or a mouthguard configured for positioning within an intraoral region of the patient. However, the accessibility to the facial region may also relate to the fact that the magnetic resonance imaging system is a dedicated scanner, configured to acquire magnetic resonance image data from a specific facial region of the patient. In accordance with an embodiment described above, the spatial coverage may be adjusted in dependence of a body model and/or a localizer measurement.

In providing accessibility to the facial region of the patient via a dedicated scanner, arbitrary optical sensors can favorably be positioned in proximity to the patient. Furthermore, a use of cumbersome mirror arrangements and/or specialized sensors suitable for magnetic fields can be avoided.

In one embodiment of the inventive method, the spatial coverage of the magnetic resonance measurement with regard to the organ structure to be imaged is adjusted (S5) by modifying a position of the at least one part of the magnetic field generator.

As described above, a dedicated scanner may be used to acquire magnetic resonance image data from the organ structure of the patient. The dedicated scanner may be limited with regard to options related to the adjustment of the spatial coverage of the magnetic resonance measurement. For example, the dedicated scanner may provide a limited selection of differently sized fields of view, such as a small field of view, a medium field of view and a large field of view. Accordingly, options for positioning the field of view within the imaging region may be limited. Adjusting the spatial coverage may comprise modifying a position and/or orientation of the magnetic resonance imaging system and/or a component of the magnetic resonance imaging system. In particular, adjusting the spatial coverage may comprise modifying a mechanical configuration of the magnetic resonance imaging system, such as a position and/or orientation the magnetic field generator, a magnet, a part of the high frequency system and/or a part of the magnetic gradient field system.

In one embodiment, the position and/or orientation of the dedicated scanner and/or components of the dedicated scanner may be modified in further dependence of a physical characteristic of the patient, a setting of the patient supporting device and/or supporting element. For example, the position and/or orientation of the magnetic field generator, a part of the high frequency system and/or a part of the gradient magnetic field system may be modified in dependence of a mouthguard or brace positioned in the intraoral region of the patient.

It is conceivable, that modifying the position and/or orientation of the at least one part of the magnetic field generator for adjusting the spatial coverage of the magnetic resonance measurement with regard to the organ structure to be imaged may be carried out in dependence of at least one of the following:

localizer image data acquired via a localizer measurement, at least one landmark detected within the localizer image data, an organ structure detected within the localizer image data, optical image data of the patient acquired via an optical sensor, a landmark detected within the optical image data.

Similar to an embodiment described above, the adjustment of the mechanical configuration of the dedicated scanner may be carried out automatically, semi-automatically or manually via the patient or the operator.

In modifying a mechanical configuration in order to adjust a spatial coverage of the magnetic resonance measurement, costs and/or spatial requirements of the dedicated scanner can favorably be reduced in comparison to conventional magnetic resonance imaging systems for clinical application.

In one embodiment, the inventive method comprises a further step of automatically validating a specific absorption rate of the magnetic resonance measurement, wherein a-priori knowledge on the patient is used to perform a first check of a setting of the specific absorption rate and wherein the specific absorption rate of the magnetic resonance measurement is adjusted if the specific absorption rate is undesirable.

A-priori knowledge on the patient may comprise any medical related information on the patient. For example, the a-priori information may comprise information on a shape, an age, a weight, a gender, a body mass index, a medical indication of the patient and the like. However, the a-priori knowledge may also comprise information on a position and/or posture of the patient, which can be acquired via an optical sensor such as a camera. It is conceivable, that a body model of the patient is determined in dependence of the a priori knowledge. The body model of the patient may comprise simple assumptions concerning the composition of the patient. For example, an inner volume of the patient may be assumed to contain water, whereas a surrounding of the patient may be assumed to contain air. In an exemplary embodiment, the body model of the patient is a 3D representation of the patient. The first check may comprise comparing a setting of the specific absorption rate as proposed by the magnetic resonance scanning protocol with a maximum specific absorption rate determined in dependence of the organ structure to be imaged and the body model of the patient. If the specific absorption rate proposed by the magnetic resonance scanning protocol exceeds the maximum specific absorption rate determined via the body model, the specific absorption rate may be updated automatically. Particularly, the setting for the specific absorption rate may be adjusted without requesting an operator interaction. For this purpose, imaging parameters of the magnetic resonance scanning protocol may be modified automatically within a permissible range. However, if the specific absorption rate cannot be solved without leaving the permissible range of an imaging parameter, a selection of alternative magnetic resonance scanning protocols comprising permissible specific absorption rates may be suggested to the operator. Thus, the operator may choose a magnetic resonance scanning protocol better suited for acquiring magnetic resonance imaging data of the organ structure of the patient.

In automatically updating the specific absorption rate of the magnetic resonance measurement or proposing alternative magnetic resonance scanning protocols, the magnetic resonance measurement may favorably be performed by an operator with lesser experience in operating magnetic resonance imaging systems, such as a dentist, an ophthalmologist, an otolaryngologist and the like. Thus, magnetic resonance imaging can favorably be introduced into medical disciplines currently having limited access to this imaging technique.

According to one embodiment, the inventive method further comprises the step performing a localizer measurement for acquiring localizer image data of the patient, wherein the ascertaining of the correct positioning of the organ structure of the patient and/or the ascertaining of the correct positioning of the magnetic resonance imaging system with regard to the positioning of the organ structure of the patient and/or the selecting of the magnetic resonance scanning protocol is carried out in dependence of the localizer image data of the patient.

In performing a localizer measurement, an information on a current position of the organ structure in the field of view of the magnetic resonance imaging device may be acquired as a reference. Based on the reference, an effort of ascertaining the correct positioning of the organ structure, ascertaining the correct positioning of the magnetic resonance imaging system and/or of selecting a magnetic resonance scanning protocol can favorably be reduced.

According to further embodiment, the inventive method comprises the step of
  providing guidance (S7) to the patient with regard to the magnetic resonance measurement, wherein
    a position of the patient is analyzed in dependence of a sensor signal indicative of a current relative position of the organ structure and the magnetic resonance imaging system and wherein
    the guidance to the patient comprises providing visual and/or audible information on at least a posture of the patient in dependence of the analyzed position of the patient.

The guidance may comprise visual and/or audible information on a posture of the patient, a position of the patient as well as an information indicative of a remaining duration of the magnetic resonance measurement. For example, the guidance may comprise an instruction on any action required to maintain the desired position of the organ structure and/or the desired position of the magnetic resonance imaging system during the magnetic resonance measurement. Visual information may be output to the patient and/or the operator via any screen, display or monitor mounted in an examination room, such as in the viewing area of the patient and/or the operator. The visual information may further be accompanied by a written dialogue and/or a voice message, such as a chatbot and the like. Accordingly, audible information may be output to the patient and/or the operator via speakers, headphones, earbuds and the like. The guidance may be provided in any phase of the magnetic resonance measurement. For example, the guidance may be provided during a preparation of the magnetic resonance measurement, during the magnetic resonance measurement and/or after the magnetic resonance measurement is completed.

In providing guidance to the patient, the patient can be enabled to support any process related to the magnetic resonance measurement. Thus, technical means to compensate for movement of the patient and/or any undesirable behavior can favorably be reduced or avoided. As a further advantage, patient comfort can be increased, as the patient can judge best if a position and/or posture is tolerable throughout a course of the magnetic resonance measurement.

In one embodiment, the inventive method comprises the step of
  automatically assessing a quality of the acquired magnetic resonance image data by evaluating at least one of a signal-to-noise ratio of the magnetic resonance image data or a presence of image artifacts within the magnetic resonance image data and outputting information on the quality of the acquired magnetic resonance image data.

The magnetic resonance imaging system may automatically evaluate a quality of the acquired magnetic resonance image data. For this purpose, a comparison with previously acquired magnetic resonance image data may be carried out. The previously acquired magnetic resonance image data may be obtained from a reference database accessible, for example, via a network connection. In one embodiment, the magnetic resonance imaging system may comprise a concurrent reading support device, for instance a software assistant, automatically comparing acquired magnetic resonance image data with image data from the reference database and informing the operator on any suspicious body regions and/or organ structures. It is also conceivable, that the magnetic resonance imaging system automatically analyzes the magnetic resonance image data in order to detect image artifacts and/or evaluate a signal-to-noise ratio of the magnetic resonance image data. The determination of the quality of the acquired magnetic resonance image data may comprise grading the magnetic resonance image data with regard to an overall image quality, a signal-to-noise ratio, a presence of image artifacts and/or a positioning of the organ structure. In an exemplary embodiment, results of the quality assessment are output to the operator on a display unit of the magnetic resonance imaging device. If the quality of the acquired magnetic resonance images is not considered to be sufficient, a subsequent magnetic resonance measurement (rescan) of the organ structure may automatically be initiated. For example, in case an image artifact is detected, the operator may automatically be informed that a rescan is prepared. In particular, the magnetic resonance system may provide proposals for adjusting imaging parameters and/or a magnetic resonance scanning protocol in order to avoid image artifacts in a subsequent magnetic resonance measurement. In an exemplary embodiment, the operator is guided through all necessary steps of setting up a rescan of the organs structure of the patient.

In automatically assessing the quality of the acquired magnetic resonance image data, the operator may be informed on the presence of image artifacts and/or a low image quality. Thus, a risk of misdiagnosing the acquired magnetic resonance image data may favorably be reduced. Furthermore, in guiding the operator through necessary steps of improving the quality of a subsequent magnetic resonance measurement, inexperienced operators may favorably be made aware of any influences that may lead to poor quality of image data. Thus, image quality and efficiency of subsequent magnetic resonance measurements may be increased.

The inventive magnetic resonance imaging system comprises a processor which is configured to coordinate and execute an inventive method by means of the magnetic resonance imaging system.

In order to acquire, process and/or store data, such as magnetic resonance image data and/or sensor signals, such as optical image data, pressure distributions, thermal images and the like, the magnetic resonance imaging system may comprise components such as a controller, a processor, a logic unit, a memory, an internal and/or an external storage unit, as well as a suitable interface configured to transmit and receive data and/or convert data into a desired data format. The processor may comprise a controller, a microcontroller, a CPU, a GPU and the like. The memory and/or the internal storage unit may comprise a RAM, ROM, PROM, EPROM, EEPROM, flash memory, as well as an HDD, an SSD and the like. However, the processor may also have access to an external database, i.e. an external server or a cloud storage, connected to the processor via a suitable network connection. The data may be transported between components via analog and/or digital signals using suitable signal connections.

In an exemplary embodiment, the magnetic resonance imaging system comprises at least one sensor configured to acquire a sensor signal indicative of a movement of a patient positioned in an imaging region of the magnetic resonance imaging system and/or a relative position between the magnetic resonance imaging system and the patient. In an exemplary embodiment, the at least one sensor is configured to transmit the sensor signal to the processor via a suitable signal connection. It is conceivable, that the processor is configured to quantify the movement of the patient and/or the relative position between the magnetic resonance imaging system and the patient in dependence of the sensor signal. The processor may further be configured to adjust a magnetic resonance scanning protocol and/or an imaging parameter of a magnetic resonance measurement and/or a localizer measurement in dependence of the sensor signal. However, the processor may also be configured to control an output unit to output a feedback regarding a positioning of the patient and/or a positioning of the magnetic resonance imaging system to the patient and/or an operator of the magnetic resonance imaging system. In an exemplary embodiment, the processor is configured to control a motor element of the magnetic resonance imaging system and/or a patient supporting system in dependence of the sensor signal according to an embodiment of the inventive method described above.

In an exemplary embodiment, the magnetic resonance imaging system comprises a dedicated scanner configured to acquire magnetic resonance image data of a specific organ structure of the patient. For example, the magnetic resonance imaging device may be configured to perform a magnetic resonance measurement of an eye region, a teeth region and/or a jaw region of the patient. Thus, an imaging volume of the magnetic resonance imaging device may be tailored to match a diagnostically relevant organ structure, such as an eye, both eyes, a tooth, several teeth, a jaw, a dental arch or both dental arches of the patient. Accordingly, an imaging region of the dedicated scanner may be configured to accommodate a body region of the patient containing the diagnostically relevant organ structure, such as a facial region, an abdominal region, a chest region, a pelvic region and/or a region comprising an extremity of the patient. In particular, the dedicated scanner may be mechanically adapted to perform cardiac imaging of a heart, mammography imaging of a breast, neurological imaging of a brain, urological imaging of a prostate, orthopedic imaging of a joint (e.g. knee, shoulder, elbow, etc.), ophthalmologic imaging of an eye, and/or dental imaging of a jaw and/or teeth of the patient.

In providing a magnetic resonance imaging system including integrated sensors, a movement and/or a positioning of the patient can be determined in a reliable and robust fashion. Furthermore, in providing a processor configured to compensate for a movement of the patient in dependence of a sensor signal, a quality of magnetic resonance image data acquired from the organ structure of the patient can be increased advantageously.

The inventive computer program product can be loaded into a memory of a programmable processor of a magnetic resonance imaging system and comprises program code means to perform a method according to the disclosure when the computer program product is executed in the processor of the magnetic resonance imaging system.

As a result, the method according to the disclosure can be carried out quickly, and in a robust and repeatable manner. The computer program product is configured in such a way that it can carry out the method steps according to the disclosure by means of the processor. The processor must in each case comprise the prerequisites, such as a corresponding main memory, a corresponding graphics card or a corresponding logic unit, so that the respective method steps can be carried out efficiently.

The computer program product is, for example, stored on a computer-readable medium or stored on a network, a server or a cloud, from where it can be loaded into the processor of a local processor. The local processor can be directly connected to the magnetic resonance imaging system or designed as part of the magnetic resonance imaging system. Furthermore, control information of the computer program product can be stored on an electronically readable medium. The control information on the electronically readable medium can be designed in such a way that, when the medium is used, it carries out a method according to the disclosure in a processor of the magnetic resonance imaging system. Examples of an electronically readable medium are a DVD, a magnetic tape or a USB stick on which electronically readable control information, in particular software, is stored. If this control information is read from the medium and stored in a control and/or processor of a magnetic resonance imaging system, all embodiments of the inventive method described above can be carried out.

FIG. 1 holds a schematic representation of an inventive magnetic resonance imaging system 10 configured to perform a magnetic resonance imaging examination of a facial region of a patient 15. The application of the magnetic resonance imaging system 10 for imaging of the jaw region of the patient 15 is to be regarded as an example. The inventive magnetic resonance imaging system 10 may also be configured to perform cardiac imaging, mammography imaging, neurological imaging, urological imaging, orthopedics imaging, ophthalmologic imaging, prostate imaging or imaging of other body regions of the patient 15. For this purpose, the magnetic field generator 13 of the magnetic resonance imaging system 10 may be positioned in proximity to a diagnostically relevant body region of the patient 15. For example, the magnetic field generator 13 may be mechanically adapted to accommodate the diagnostically relevant body region of the patient 15 in such a way, that a contour of the magnetic field generator matches a contour of the diagnostically relevant body region of the patient 15.

The magnetic resonance imaging system 10 comprises a magnetic field generator 13 and an imaging region 14 configured to receive an examination object 15, for example the jaw region of the patient 15. The imaging region 14 is at least partially enclosed by the magnetic field generator 13. The patient 15 may access the imaging region 14 by means of a patient supporting device 16. However, the magnetic resonance imaging system 10 may comprise a positioning system 11 including adjustment means 12 for adjusting a position and/or an orientation of the magnetic field generator 13 with respect to the patient 15. In one example, the adjustment means 12 may comprise a swivel joint configured to rotate the magnetic field generator 13 along a rotation direction Wx and a rotation direction Wy. A position of the magnetic field generator 13 along a Y-direction and a Z-direction may be adjusted via a suitable telescope system and/or rail system integrated within the positioning system 11. Of course, other embodiments of the positioning system 11 and the adjustment means 12 are conceivable. In one embodiment, the patient supporting device 16 may comprise further adjustment means 18 configured to position at least a body part of the patient 15 and/or support at least a body part of the patient 15 in a desired position.

The magnetic field generator 13 comprises at least one magnet 17 configured to generate a magnetic field in the imaging region 14. The magnetic field generator 13 may further include a magnetic field gradient system (not shown) comprising gradient coils 28 for generating magnetic gradient fields used for spatial encoding of magnetic resonance signals acquired during a magnetic resonance measurement. In an exemplary embodiment, the magnetic field generator 13 further comprises a high frequency system including at least one radiofrequency antenna (not shown). The radiofrequency antenna may be configured to emit a radiofrequency excitation pulse in the imaging region 14 and/or receive magnetic resonance signals from the imaging region 14.

In order to control the magnetic field generator 13 as well as the radiofrequency antenna, the magnetic resonance imaging system 10 comprises a controller 20. The controller 20 is configured to control the magnetic resonance imaging system 10 to perform a magnetic resonance measurement. For this purpose, the controller 20 may comprise a signal connection with a gradient controller 21 and a radiofrequency antenna controller 22. It is also conceivable, that the gradient controller 21 and the radiofrequency antenna controller 22 are integrated in the controller 20. Furthermore, the controller 20 may comprise a processor 24 configured to coordinate an acquisition and/or an evaluation of magnetic resonance signals acquired from the imaging region 14. It is conceivable, that the processor 24 is also configured to evaluate data such as magnetic resonance signals and/or magnetic resonance image data. In particular, the processor 24 may be configured to process sensor signals from sensors 40, such as pressure sensors 40a and/or optical sensors 40b, integrated within the patient supporting device 16. The controller 20 may comprise a processor, a microcontroller, an analog circuit, a logic unit and the like. The processor 24 may comprise a processor, such as a CPU, a GPU and the like. It is also conceivable, that the controller 20 and/or the processor 24 comprise a memory and/or an internal storage, such as a RAM, a ROM, a PROM, an EPROM, an EEPROM, a flash memory, as well as an HDD, an SSD and the like. It is conceivable, that the processor 24 is connected to an external database 29 via a network connection. The external database 29 may be a medical database comprising patient information and/or a reference database comprising information related to a body model and/or an organ model of the patient 15 and/or the magnetic resonance imaging system 10. In particular, the external database 29 may be connected to a radiological information system and/or a hospital information system. In an exemplary embodiment, the controller 20 includes processor circuitry that is configured to perform one or more functions and/or operations of the controller 20.

The magnetic resonance imaging system 10 may further comprise at least one output unit 25 configured to output information, such as control commands, instructions on a correct positioning of the magnetic resonance imaging system 10, instructions on a correct position and/or posture of the patient 15, but also imaging parameters and/or magnetic resonance image data. The output unit 25 may comprise a monitor configured to output visual information to an operator and/or a patient 15. However, the output unit 25 may also comprise a speaker configured to output audible information to the operator and/or the patient 15. In one embodiment, the output unit 25 may be a control element configured to directly transmit control commands to the positioning system 11 and/or adjustment means 12. In an exemplary embodiment, the magnetic resonance imaging system 10 comprises a plurality of output units 25, for example at least one monitor, at least one speaker and/or at least one control element.

The magnetic resonance imaging system 10 may further comprise an input unit 26 configured to receive information and/or parameters by the operator during a magnetic resonance imaging examination.

As shown in FIG. 1, the patient supporting device 16 comprises a plurality of pressure sensors 40a, such as strain gauges and/or capacitive, electromagnetic or piezoelectric pressure sensors, in order to acquire a pressure distribution exerted by the patient 15 on the patient supporting device 16. The pressures sensors 40a may transmit sensor signals to the processor 24, which is configured to determine a current position and/or posture of the patient 15 on the patient supporting device 16 in dependence of the sensor signals. If the current position and/or posture of the patient 15 does not match a desired position and/or posture of the patient 15 within a predefined acceptance range, the processor 24 and/or the controller 20 may output control commands to motor elements (not shown) of the patient supporting device 16 via the output unit 25. Thus, the position of the patient supporting device 16 may automatically be adjusted to correct the position and/or posture of the patient 15. However, it is also conceivable, that instructions regarding the positioning of the patient 15 and/or the magnetic resonance imaging system 10 are visually output on a monitor in the examination room.

The illustrated magnetic resonance imaging system 10 may of course include further components that magnetic resonance imaging systems 10 usually comprise. The general mode of operation of a magnetic resonance imaging system 10 is well-known to the person skilled in the art, so a further description of the general components or a sequencing of a magnetic resonance imaging examination is not deemed necessary.

FIG. 2 depicts a further embodiment of a magnetic resonance imaging system 10 according to the disclosure. The magnetic resonance imaging system 10 comprises a C-shaped magnet arrangement 30 partially encompassing the head of the patient 15 in a circumferential direction. The imaging volume 19 provided by the magnetic field generator 13 is positioned in the eye region of the patient 15. It is conceivable, that the magnetic resonance imaging system 10 and/or components of the magnetic resonance imaging system 10 may be moved relative to the patient 15 along the Z-direction, the Y-direction and/or the X-direction in order to adjust the position of the imaging volume 19 to a diagnostically relevant region of the patient 15. It is also conceivable, that the magnetic resonance imaging system 10 and/or its components may be tilted or turned with respect to the patient 15.

In one example, a diagnostically relevant region may comprise the jaw region of the patient 15. In an exemplary embodiment, the magnet arrangement 30 is configured in such a way, that a shape of the imaging region 14 is matched with an organ structure of the patient 15 to be imaged. For covering a dental arch of the patient 15, the imaging volume 19 may comprise an ellipsoid shape. In other examples, the shape of the imaging volume 19 may be ovoid, polygonal, prismatic or any combination thereof. In FIG. 2, the imaging volume 19 comprises an ellipsoid shape in order to cover both eyes of the patient 15 during the magnetic resonance measurement. However, the magnet arrangement 30 may also be configured to provide an approximately spherical isocenter 19 which covers only one eye of the patient 15.

In the depicted embodiment, the magnetic resonance imaging system 10 comprises two cameras 40b, which are configured to acquire optical image data from the eyes of the patient 15. The cameras 40a are oriented in such a way, that optical image data of the eyes, particularly of the pupils, can be acquired. The acquired optical image data is transmitted to the processor 24 of the magnetic resonance imaging system 10 via a suitable signal connection. For example, the image data may comprise analog and/or digital signals transferred via a cable connection or a wireless connection such as WLAN, Bluetooth, infrared and so forth. In order to reduce a movement of the patient 15 during the magnetic resonance measurement, the head of the patient 15 is positioned in a headrest 32. The headrest 32 may be configured to suppress tilting and/or turning of the head. For this purpose, the head of the patient 15 may also be fixed in the headrest via suitable fasteners (not shown). Furthermore, the arrangement of the magnetic field generator 13 provides an accessibility to the facial region of the patient 15. Thus, optical sensors 40b may be used to acquire optical image data from the facial region of the patient 15 while the patient 15 is positioned within the imaging region 14 of the magnetic resonance imaging system 10.

FIG. 3 shows front view of a facial region of the patient 15 positioned in the imaging acquisition region 14 of the magnetic resonance imaging system 10 shown in FIG. 2. The facial region of the patient 15 comprises a plurality of landmarks 41, such as the contour of eyebrows, the mouth or the tip of the chin, the nose or the ears. The processor 24 may be configured to detect landmarks 41 in the optical image data acquired via the cameras 40b in order to determine the position the organ structure to be imaged. In the shown example, the organ structure to be imaged is the jaw region of the patient 15, which is directly accessible via the cameras 40b. However, the position of organ structures not accessible via optical sensors may be determined in dependence of a body model of the patient 15.

As described above, the magnetic resonance imaging system 10 and/or components of the magnetic resonance imaging system 10 may be adjusted, for example to match the position of the imaging volume 19 with the jaw region of the patient 15. For this purpose, the magnetic field generator 13, a part of the high frequency system and/or a part of the magnetic field gradient system may be moved and/or tilted with respect to the patient 15. In one embodiment, a distance between two magnets 17a and 17b and/or two gradient coils 28a and 28b may be adjusted, in order to better accommodate the patient 15 and/or match the imaging volume 19 with the organ structure to be imaged. In a further embodiment, a position and/or orientation of the magnetic field generator 13, the magnetic field gradient system and/or the high frequency system, particularly a radiofrequency receiving antenna, is adjusted via the positioning system 11 and/or adjustment means 12 in order to compensate for a movement of the patient 15.

FIG. 4 depicts a schematic flowchart of an iterative adjustment of the field of view 50 of the magnetic resonance measurement according to an embodiment of the inventive method. In an iteration step $I_0$, first localizer image data of the organ structure 51 is acquired with an estimated field of view 50a. The estimated field of view 50a may have been determined in dependence of
- a sensor signal indicative of a patient position and/or posture,
- optical image data of the patient 15,
- a landmark 41 of the patient 15 detected via a sensor and/or a localizer measurement or
- a body model of the patient 15 according to an embodiment described above. For example, the organ structure 51 to be imaged may be enriched with a contrast agent in order to provide a landmark 41. Thus, differentiating the organ structure 51 from a surrounding tissue in the first localizer image data may be facilitated. As shown in FIG. 4, the organ structure 51 may partially be positioned outside of the field of view 50a. In order to improve a positioning of the field of view 50a, a bounding box 52a may be determined enclosing the organ structure 51. As the organ structure 51 is partially positioned outside the field of view 50a, a missing section of the organ structure 51 may be determined, e.g. by using a body model of the patient and/or an anatomical model of the organ structure 51. In dependence of the missing section of the organ structure 51, a field of view 50b may be determined, for example by shifting the field of view 50a in an expected direction of the missing section of the organ structure 51.

Subsequently, a second localizer measurement may be carried out to acquire second localizer image data of the organ structure 51. In a step $I_b$, the field of view 50b may enclose the organ structure 51 entirely. In order to improve the spatial coverage of the organ structure 51, a bounding box 52b may be determined, e.g. by segmenting the organ structure 51 and/or using other image processing techniques. The bounding box 52 may be tailored in such a way, that a volume of surrounding tissue and/or other matter irrelevant to a diagnosis of the organ structure 51 is reduced. At this stage, a field of view 50c may be determined, which may correspond to the bounding box 52b. The magnetic resonance measurement may subsequently be carried out in order to acquire magnetic resonance image data of the organ structure 51. The magnetic resonance image data may comprise an enhanced spatial coverage of the organ structure 51 as shown in $I_c$ of FIG. 4.

FIG. 5 shows a flowchart of an inventive method for performing a magnetic resonance measurement of the organ structure 51 of the patient 15 using a magnetic resonance imaging system 10 particularly adapted to the imaging of such organ structure 51.

In a step S1, a correct positioning of the organ structure 51 of the patient 15 is ascertained for the magnetic resonance measurement.

In one embodiment, ascertaining the correct position of the patient 15 comprises using an array of pressure sensors 40a and/or a camera 40b to acquire sensor signals indicative of a current position and/or posture of the patient 15. The current position and/or posture of the patient 15 and a desired position and/or posture of the patient 15 may be analyzed by the processor 24 in order to derive a difference between the current position and/or posture of the patient 15 and the desired position and/or posture of the patient 15. The desired position and/or posture of the patient 15 may be different on the organ structure 51 to be imaged and may be determined in dependence of a scanning prescription, a referral, information obtained from a reference database 29, a manual input from an operator and/or a body model of the patient 15.

Ascertaining the correct positioning of the organ structure 51 of the patient 15 for the magnetic resonance measurement may comprise outputting a feedback regarding the difference between the current position and/or posture of the patient 15 and the desired position and/or posture of the patient 15 via an output unit 25, such as a projector, a monitor and/or a speaker. The feedback may comprise an audible and/or visual instruction on how to improve the position and/or posture of the patient 15. In an exemplary embodiment, the feedback is directed to the patient 15. Thus, the patient 15 is able to adapt the current position and/or posture in accordance with the feedback.

However, in order to reduce the difference between the current position and/or posture of the patient 15 and the desired position and/or posture of the patient, adjustment means of the patient supporting device 16 may automatically be adjusted, thus improving the position of the patient 15 for the magnetic resonance measurement. For example, the controller 20 may output a control command to a motor element of the patient supporting device 16 in order to increase a height of the patient 15. Thus, a height of organ structure 51 to be imaged may be increased with respect to the magnetic resonance imaging system 10.

In a step S2, a correct positioning of the magnetic resonance imaging system 10 with regard to the positioning of the organ structure 51 of the patient 15 is ascertained.

Similar to the step S1, a sensor signal indicative of a relative position between the patient 15 and the magnetic resonance imaging system 10 may be acquired via a sensor 40. In an exemplary embodiment, a difference between a current relative position between the magnetic resonance imaging system 10 and the patient 15 and a desired relative position between the magnetic resonance imaging system 10 and the patient 15 may be determined via the processor 24 in dependence of the sensor signal. Subsequently, a required adjustment of a position and/or orientation of the magnetic resonance imaging system 10 is determined in dependence of the difference.

Based on the required adjustment, a control command may be output to the positioning system 11 and/or the adjustment means 12 of the magnetic resonance imaging system 10 and/or patient supporting device 16, thus automatically adjusting a position and/or orientation of the patient 15 and/or the magnetic resonance imaging system 10. For example, a motor element of the positioning system 11 may be controlled to shift the magnetic resonance imaging system 10 along the Z-direction towards the patient 15. Thus, the imaging volume 19 of the magnetic resonance imaging system 10 may be relocated towards the organ structure 51 within the patient 15.

In one embodiment, the ascertaining of the correct positioning of the magnetic resonance imaging system 10 with regard to the positioning of the organ structure 51 of the patient 15 comprises adjusting a position of at least a part of a magnetic field generator 13 of the magnetic resonance imaging system 10. As shown in FIG. 1, a position of the magnetic field generator 13 may be adjusted by controlling the adjustment means 12 and/or the positioning system 11 via a control command provided by the controller 20 and/or the processor 24 in dependence of the required adjustment. Individual parts of the magnetic field generator 13 may be adjusted independently of one another or of other components of the magnetic resonance imaging system 10.

The ascertaining of the correct positioning of the magnetic resonance imaging system 10 with regard to the positioning of the organ structure 51 of the patient 15 may comprise acquiring a sensor signal indicative of a current relative position between the organ structure 51 and at least one reference point of the magnetic resonance imaging system 10 and determining a required modification to the positioning of the magnetic resonance imaging system 10 in dependence of the sensor signal indicative of the current relative position between the organ structure 51 and the at least one reference point of the magnetic resonance imaging system 10, wherein the position of the at least one part of the magnetic field generator 13 is adjusted in dependence of the required modification. The reference point may be, for example, a center of the imaging volume 19, a predefined geometrical location of the magnetic resonance imaging system 10 as well as a colored marker and/or a reflective marker positioned on a surface of the magnetic resonance imaging system 10. However, the reference point may also be a position of the sensor 40 configured to acquire the sensor signal indicative of the current relative position of the organ structure 51 and the at least one reference point. Particularly when using non-optical sensors 40, a body model of the patient 15 and/or a geometric model of the magnetic resonance imaging system 10 may be used in order to determine the required modification to the positioning of the magnetic resonance imaging system 10. The required modification may comprise adjusting a position and/or orientation of a magnet 17, a radiofrequency emitting antenna, a radiofrequency receiving antenna, and/or the gradient coil 28 as described above.

In one embodiment, the ascertaining of the correct positioning of the magnetic resonance imaging system 10 with regard to the positioning of the organ structure 51 of the patient 15 comprises acquiring an information indicative of a physical characteristic of the patient 15 and/or an imaging situation and determining a required modification to the positioning of the magnetic resonance imaging system 10 in dependence of the physical characteristic of the patient 15 and/or the imaging situation, wherein the position of the at least one part of the magnetic field generator 13 is adjusted in dependence of the required modification. Information indicative of a physical characteristic of the patient 15 may be determined via suitable sensors 40 and/or be obtained from a medical prescription, a referral and/or a medical database comprising patient information. The imaging situation may relate to screening or imaging of a specific organ structure 51 in context of differential diagnosis, therapy, intervention and the like. For instance, the imaging situation may be obtained from a scanning prescription of the patient 15. According to the imaging situation and/or the physical characteristic of the patient 15, different requirements related to an accuracy of the correct positioning of the magnetic resonance imaging system 10 and/or an available time allocation may be met when performing the magnetic resonance measurement.

According to an optional step S3, a localizer measurement for acquiring localizer image data of the patient 15 is performed. For example, the localizer measurement may comprise a projection measurement or a navigator measurement of the patient 15 or the body region of the patient 15 containing the organ structure 51 to be imaged. The localizer measurement may be carried out in dependence of preliminary imaging parameters, such as an estimated field of view and/or an estimated position of the organ structure 51. The preliminary imaging parameters may be derived in dependence of the organ structure 51 to be imaged, a scanning prescription and/or a referral. However, preliminary imaging parameters dependent on the organ structure 51 may also be selected manually or derived in dependence of sensor signals and/or a body model of the patient 15.

A step S4 comprises selecting a magnetic resonance scanning protocol for performing the magnetic resonance measurement of the organ structure 51. In an exemplary embodiment, the selection of the scanning protocol is carried out automatically in dependence of a scanning prescription of the patient 15 and/or a referral of a physician. For example, the processor 24 may determine a potentially fitting magnetic resonance scanning protocol in dependence of the scanning prescription, the referral and/or the requested body region of the patient 15. However, it is also conceivable to manually select the magnetic resonance scanning protocol based on a pre-selection of potentially fitting magnetic resonance scanning protocols provided by the magnetic resonance imaging system 10. The pre-selection of magnetic resonance protocols may be presented to the operator for selection via the output unit 25.

Further embodiments may comprise performing a localizer measurement and/or acquiring optical image data of the patient 15, particularly of the eye region and/or the jaw region of the patient 15. In these cases, a tooth and/or an eye of the patient 15 may directly be detected in the optical image data and/or be detected as landmarks 41 within the localizer image data acquired via the localizer measurement. Ascertaining the correct positioning of the magnetic resonance imaging system 10 with regard to the positioning of the organ structure 51 of the patient 15 may thus comprise adjusting the position of at least one part of the magnetic field generator 13 in dependence of a tooth and/or an eye detected in the optical image data and/or a landmark 41 within localizer image data.

According to a step S5, a spatial coverage of the magnetic resonance measurement is adjusted with regard to the organ structure 51 to be imaged.

For example, the spatial coverage of the magnetic resonance measurement may be determined in dependence of optical image data of the patient 15 acquired via a camera and/or other optical sensor 40. Using an optical sensor 40 is particularly convenient if the body region of the patient 15 containing the organ structure 51 to be imaged is easily accessible with optical imaging. For example, an easily accessible body region may be the head region of the patient 15, particularly the eye region, the jaw region and/or the teeth region. The camera and/or optical sensor 40 may track facial landmarks 41 of the patient 15, such as an eye, an eyebrow, a nose, a lip, a chin, a mouth, a cheekbone and the like. The spatial coverage may be determined based on an absolute position and/or a relative position of facial landmarks 41 tracked via the optical sensor 40.

In one embodiment, a sensor signal indicative of a position and/or posture of the patient 15 is acquired, wherein the adjusting of the spatial coverage of the magnetic resonance measurement with regard to the organ structure 51 to be imaged comprises an iterative adjustment of a field of view 50 of the magnetic resonance measurement in dependence of a body model of the patient 15 and the sensor signal indicative of the position and/or posture of the patient 15. The sensor signal indicative of the position and/or posture of the patient may be acquired via at least one of an optical sensor, a distance sensor, a position sensor of a radiofrequency receiver, a pressure sensor and/or a thermal sensor. As shown in FIG. 4, an estimated field of view 50a may be determined in dependence of the body model of the patient 15 in a first iteration step $I_a$. After performing a first localizer measurement or first magnetic resonance measurement of the specific organ structure 51 of the patient 15, the position of the specific organ structure 51 may be detected and the position of the boundary box 52a may be refined. For the second iteration step $I_b$, a second field of view 50b may be determined in dependence of a position of the organ structure 51 within the first localizer image data. Subsequently, a second localizer measurement or second magnetic resonance measurement may be carried out to validate the position of the organ structure 51 within the second localizer image data. If the organ structure 51 is enclosed within the second localizer image data, the boundary box 52b may be further refined to reduce the volume of diagnostically irrelevant tissue surrounding the organ structure 51 to determine the field of view 50c of the magnetic resonance measurement in step $I_c$. It is conceivable, that the organ structure 51 is already enclosed within the field of view 50a when performing the first localizer measurement in the iteration step $I_a$. In this case, the field of view 50c for the magnetic resonance measurement may directly be determined in dependence of the first localizer image data.

According to one embodiment, a landmark 41 is detected in the localizer image data, wherein the landmark 41 is a tooth and/or an eye of the patient 15 and wherein the adjusting of the spatial coverage of the magnetic resonance measurement with regard to the organ structure 51 to be imaged is carried out in dependence of the landmark 41 in the localizer image data. In order to detect a tooth and/or an eye of the patient 15 as a landmark 41, the imaging parameters of the localizer measurement may be specifically adapted to provide a high or low contrast of a tooth and/or an eye of the patient 15. In an embodiment, both a tooth and an eye of the patient 15 are detected as landmarks 41 via a single localizer measurement. In an exemplary embodiment, the imaging parameters of the localizer measurement are adapted to provide a high contrast of the eye of the patient 15. Thus, the tooth may be detected as a landmark 41 due to its lack of magnetic resonance signal. The detected landmarks 41 may be used to determine a position and/or posture of the patient 15 as well as a position of the organ structure 51 to be imaged according an embodiment described above. Accordingly, the spatial coverage of the magnetic resonance measurement may be adjusted automatically, semi-automatically or manually.

In a further embodiment, the organ structure 51 is segmented in the localizer image data, wherein the spatial coverage of the magnetic resonance measurement is automatically adjusted in dependence of a position of the organ structure 51 within the localizer image data if the organ structure 51 is enclosed within the localizer image data or wherein a subsequent localizer measurement for acquiring subsequent localizer image data is performed if at least a part of the organ structure 51 is positioned outside of the localizer image data and wherein the spatial coverage of the magnetic resonance measurement is automatically adjusted in dependence of a position of the organ structure 51 within the subsequent localizer image data. In an exemplary embodiment, the organ structure 51 is roughly segmented in such a way, that an examination of the spatial coverage of the organ structure 51 is still possible.

For examining the spatial coverage of the organ structure 51, it may be verified if the organ structure 51 is entirely captured in the localizer image data and/or if the organ structure could be segmented completely. If this is not the case, a subsequent localizer measurement may be performed in order to refine the spatial coverage. For example, if the organ structure is not fully captured in the localizer image data, the field of view 50 may be increased and/or shifted to better cover the organ structure 51. However, adjusting the spatial coverage may also comprise adjusting a spatial resolution of the organ structure 51, e.g. with respect to a spatial resolution required for diagnosing a suspected disease. For example, in adjusting the field of view 50 to reduce diagnostically irrelevant tissue, the spatial resolution of the organ structure 50 may be increased without increasing the time required for performing the magnetic resonance measurement.

In a further embodiment, the organ structure 51 is at least one tooth or at least one eye of the patient 15, wherein optical image data of the at least one eye or a jaw region comprising the at least one tooth is acquired via an optical sensor 40 and wherein the spatial coverage of the magnetic resonance measurement with regard to the at least one tooth or the at least one eye is automatically adjusted in dependence of the optical image data. For acquiring optical image data from a jaw region or an eye of the patient 15, an accessibility to a facial region of the patient 15 may be exploited. The accessibility to the facial region of the patient 15 may be provided via a clearance between the facial region of the patient 15 and the optical sensor 40 as depicted in FIG. 2. The accessibility may further comprise a clearance for a mechanical element, such as a fixation element and/or a mouthguard 54 configured for positioning within an intraoral region of the patient 15. In accordance with an embodiment described above, the spatial coverage may also be adjusted in dependence of a body model and/or a localizer measurement.

According to a further embodiment, the spatial coverage of the magnetic resonance measurement with regard to the organ structure 51 to be imaged is adjusted by modifying the position of the at least one part of the magnetic field generator 13 of the magnetic resonance imaging system 10. For this purpose, a mechanical configuration of the magnetic resonance imaging system 10 may be modified. In an exemplary embodiment, the magnetic resonance imaging system 10 is a dedicated scanner mechanically adapted to fit a body region of the patient 15 containing the organ structure 51 to be imaged as shown in FIG. 1 and FIG. 2. For example, the dedicated scanner may comprise a selection of available fields of view depending on the mechanical configuration. In Particular, modifying the mechanical configuration of the dedicated scanner may comprise modifying a position and/or an orientation of a magnet 17, a radiofrequency emitting antenna, a radiofrequency receiving antenna and/or a gradient coil 28 via the positioning system 11 and/or the adjustment means 12. Modifying the position and/or orientation of the at least one part of the magnetic field generator 13 for adjusting the spatial coverage of the magnetic resonance measurement with regard to the organ structure 15 may be carried out in dependence of at least one of the following:

- localizer image data acquired via a localizer measurement,
- at least one landmark 41 detected within the localizer image data,
- an organ structure 51 detected within the localizer image data,
- optical image data of the patient 15 acquired via an optical sensor,
- a landmark 41 detected within the optical image data.

A step S6 comprises performing the magnetic resonance measurement to acquire magnetic resonance image data of the organ structure 51. The magnetic resonance measurement may be started automatically once requirements of the preceding steps have been fulfilled. However, actions related to one or more of the previously described steps and/or embodiments may continue throughout the magnetic resonance measurement. The magnetic resonance measurement may be started via an input of the operator to the input unit 26. However, the magnetic resonance measurement may also be initiated automatically or semi-automatically, for example in reaction to a confirmation from the operator.

In an optional step S7, guidance is provided to the patient 15 with regard to the magnetic resonance measurement, wherein a position of the patient 15 is analyzed in dependence of a sensor signal indicative of a current relative position of the organ structure 51 and the magnetic resonance imaging system 10 and wherein the guidance to the patient 15 comprises providing visual and/or audible information on at least a posture of the patient 15 in dependence of the analyzed position of the patient 15.

When the patient 15 enters the examination room of the magnetic resonance imaging system 10, the patient 15 may be recognized via suitable sensors 40, such as cameras and/or pressure sensors integrated into a patient supporting device 16. As a consequence, an instruction video on how to correctly position oneself within the imaging region 14 of the magnetic resonance imaging system 10 and/or behave correctly during the magnetic resonance measurement may be played back on a display of a monitor 25.

With aid of the available sensors 40, e.g. an optical sensor and/or a pressure sensor, the magnetic resonance imaging system 10 may detect that the patient 15 has taken place within the imaging region 14 or in proximity to the imaging region 14. The magnetic resonance imaging system 10 may then provide further and/or more detailed instructions on the correct positioning of the patient 15 and/or a specific posture required for the magnetic resonance measurement. This procedure may continue until the patient 15 is placed in the desired position and/or the desired posture for the examination. Thus, constant guidance may be provided to the patient 15, analyzing the patient's position and/or posture, comparing a current patient's position and/or posture to a desired position and/or posture and instructing the patient 15 on how to improve the position and/or posture. In case the patient 15 leaves the desired position/or posture, the magnetic resonance system may provide direct instructions on what adjustments to the current position and/or posture are required to restore the desired position and/or posture. In an exemplary embodiment, a direct instruction comprises a voice message, such as "Please move your chin more upwards" or "Please turn your head slightly to the left". The guidance may also comprise reminding the patient 15 to remain in the desired position until the magnetic resonance measurement is completed.

It is also conceivable, that the desired position of the patient 15 comprises an acceptance range characterizing a permissible deviation from a desired position and/or posture. In this case, guiding the patient 15 may comprise informing the patient 15 when the patient 15 is about to leave the acceptance range.

The magnetic resonance imaging system 10 may also inform the patient 15 on a progress the of magnetic resonance measurement. This information may comprise details on upcoming magnetic resonance measurements (e.g. localizer measurements, subsequent localizer measurements and/or measurements of further organ structures) as well as on a remaining duration of the magnetic resonance measurement and/or upcoming magnetic resonance measurements. Furthermore, the magnetic resonance imaging system 10 may comprise a projector 25 for guiding the patient to occupy the desired position. The projector 25 may project the desired position and/or posture on the patient supporting device 16, such as a patient chair, a patient table or a patient stand.

The magnetic resonance imaging system 10 may constantly monitor the position and/or posture of the patient 15 during preparation of the magnetic resonance measurement, while conducting the magnetic resonance measurement and/or after completion of the magnetic resonance measurement. The latter may comprise, for example, information on a location of a waiting room, an estimated waiting time and/or a subsequent examination to be performed.

According to a further optional step S8, a quality of the acquired magnetic resonance image data is automatically assessed by evaluating at least one of a signal-to-noise ratio of the magnetic resonance image data or a presence of image artifacts within the magnetic resonance image data and outputting information on the quality of the acquired magnetic resonance image data.

FIG. 6 holds a depiction of a graphical representation of the patient 53. The graphical representation of the patient 53 may be used to indicate the scanning prescription, the imaging situation, the pre-selection of magnetic resonance scanning protocols, as well as a target body region of the patient 15 and/or a field of view 50 of the localizer measurement and/or the magnetic resonance measurement. In the example shown in FIG. 6, screening of the prostate of the patient 15 is selected from a drop-down menu providing a pre-selection of magnetic resonance measurements to the operator for selection. Thus, a field of view 50 is shown in order to indicate the body region of the patient 15 to be imaged. The drop-down menu is intentionally shortened and may of course comprise further entries according to an embodiment described above. It is also conceivable, that the graphical representation of the patient 15 comprises a real-time representation of the current position and/or posture of the patient 15 in relation to the field of view 50 and/or the magnetic resonance imaging system.

FIG. 7 shows a schematic representation of a dedicated scanner, e.g. for imaging of teeth, eyes and/or the prostate of the patient 15. The dedicated scanner comprises a triangular shape with two magnets 17a and 17b and two gradient coils 28a and 28b. The field of view 50 is positioned in a corner of the triangular shaped dedicated scanner. According to a mechanical configuration of the dedicated scanner and/or an imaging parameter, the dedicated scanner may comprise differently sized fields of view 50a and 50b, which may be adjusted according to an embodiment described above. For example, adjusting the mechanical configuration of the dedicated scanner may comprise adjusting an angle between the two magnets 17a and 17b. For imaging of the prostate, the triangular shaped dedicated scanner, may be oriented like a chair for the patient 15 to sit upon. Thus, the dedicated scanner is mechanically adapted to fit a specific body region of the patient 15 containing the organ structure 51 to be imaged. Of course, the dedicated scanner may comprise other shapes, such as a saddle-shape or an asymmetrical shape in order to fit the specific body region of the patient 15.

In an exemplary embodiment, the pre-selection of magnetic resonance scanning protocols is displayed to the operator in conjunction with a graphical representation, such as a patient avatar and/or a pre-view of images/orientation The embodiments described above are to be recognized as examples. Individual embodiments may be extended by features of other embodiments. In particular, a sequence of the steps of the inventive methods are to be understood as exemplary. The individual steps can also be carried out in a different order as described above and/or overlap partially or completely in time.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for performing a magnetic resonance (MR) measurement of an organ structure of a patient using a magnetic resonance imaging (MRI) system configured for imaging of the organ structure, the method comprising:
    ascertaining, via a processor, a correct positioning of the organ structure of the patient for the MR measurement;
    ascertaining a correct positioning of the MRI system with regard to the positioning of the organ structure of the patient, by acquiring, via the processor: a sensor signal indicative of a current relative position between the organ structure and at least one reference point of the MRI system, information indicative of a physical characteristic of the patient, and/or localizer image data of the patient, wherein the ascertaining of the correct positioning of the MRI system with regard to the positioning of the organ structure of the patient includes: performing a localizer measurement to acquire the localizer image data of the patient, and detecting a landmark within the localizer image data, the landmark being a tooth and/or an eye of the patient;
    determining, via the processor, a required modification to the positioning of the MRI system based on the acquired sensor signal, the acquired information, and/or the acquired localizer image data;
    automatically adjusting, via the processor, a position of at least one part of a magnetic field generator of the MRI system based on the required modification and the detected landmark;
    selecting, via the processor, a MR scanning protocol for performing the MR measurement of the organ structure;
    adjusting, via the processor, a spatial coverage of the MR measurement with regard to the organ structure to be imaged; and
    controlling, via the processor, the MRI system to perform the MR measurement to acquire MR image data of the organ structure.

2. The method according to claim 1, wherein the ascertaining of the correct positioning of the MRI system with regard to the positioning of the organ structure of the patient comprises:
    acquiring information indicative of an imaging situation, wherein the determining the required modification to the positioning of the MRI system is further based on the imaging situation.

3. The method according to claim 1, further comprising:
    providing guidance to the patient with regard to the MR measurement, wherein:
        a position of the patient is analyzed based on a sensor signal indicative of a current relative position of the organ structure and the MRI system, and
        the guidance to the patient comprises providing visual and/or audible information on at least a posture of the patient based on the analyzed position of the patient.

4. A non-transitory computer program product which includes a program and is directly loadable into a memory of the MRI system, when executed by a processor of the MRI system, causes the processor to perform the method as claimed in claim 1.

5. A non-transitory computer-readable storage medium with an executable program stored thereon, that when executed, instructs a processor to perform the method of claim 1.

6. The method according to claim 1, wherein:
    ascertaining the correct positioning of the MRI system with regard to the positioning of the organ structure of the patient comprises: acquiring, via the processor, the sensor signal indicative of the current relative position between the organ structure and the at least one reference point of the MRI system, the information indicative of the physical characteristic of the patient, and the localizer image data of the patient; and
    determining the required modification comprises determining, via the processor, the required modification to the positioning of the MRI system based on the acquired sensor signal, the acquired information, and the acquired localizer image data.

7. A method for preforming a magnetic resonance (MR) measurement of an organ structure of a patient using a magnetic resonate imaging (MRI) system configured for imaging of the organ structure, the method comprising:
    ascertaining, via a processor, a correct positioning of the organ structure of the patient for the MR measurement, wherein the organ structure is at least one tooth or at least one eye of the patient;

ascertaining a correct positioning of the MRI system with regard to the positioning of the organ structure of the patient, by acquiring, via the processor: a sensor signal indicative of a current relative position between the organ structure and at least one reference point of the MRI system, information indicative of a physical characteristic of the patient, and/or localizer image data of the patient, wherein the ascertaining of the correct positioning of the MRI system with regard to the positioning of the organ structure of the patient including acquiring optical image data, via an optical sensor, of the at least one eye and/or a jaw region including the at least one tooth;

determining, via the processor, a required modification to the positioning of the MRI system based on the acquired sensor signal, the acquired information, and/or the acquired localizer image data;

automatically adjusting, via the processor, a position of at least one part of a magnetic field generator of the MRI system based on the required modification and the acquired optical image data;

selecting, via the processor, a MR scanning protocol for performing the MR measurement of the organ structure;

adjusting, via the processor, a spatial coverage of the MR measurement with regard to the organ structure to be imaged; and controlling, via the processor, the MRI system to perform the MR measurement to acquire MR image data of the organ structure.

8. A method for performing a magnetic resonance (MR) measurement of an organ structure of a patient using a magnetic resonance imaging (MRI) system configured for imaging of the organ structure, the method comprising:

ascertaining, vis a processor, a correct positioning of the organ structure of the patient for the MR measurement;

ascertaining a correct positioning of the MRI system with regard to the positioning of the organ structure of the patient, by acquiring, via the processor: a sensor signal indicative of a current relative position between the organ structure and at least one reference point of the MRI system, information indicative of a physical characteristic of the patient, and/or localizer image data of the patient;

determining, via the processor, a required modification to the positioning of the MRI system based on the acquired sensor signal, the acquired information, and/or the acquired localizer image data;

automatically adjusting, via the processor, a position of at least one part of a magnetic field generator of the MRI system based on the required modification;

selecting, via the processor, a MR scanning protocol for performing the MR measurement of the organ structure;

acquiring a sensor signal indicative of a position of the and/or posture of the patient;

adjusting, via the processor, a spatial coverage of the MR measurement with regard to the organ structure to be imaged, wherein the adjusting of the spatial coverage of the MR measurement with regard to the organ structure to be imaged includes an iterative adjustment of a field of view of the MR measurement based on a body model of the patient and the sensor signal indicative of the position and/or posture of the patient; and controlling, via the processor, the MRI system to perform the MR measurement to acquire MR image data of the organ structure.

9. The method according to claim 8, wherein the sensor signal includes data from an optical sensor, a distance sensor, a position sensor, a pressure sensor, and/or a thermal sensor.

10. The method according to claim 8, wherein the spatial coverage of the MR measurement with regard to the organ structure to be imaged is adjusted by modifying a position of the at least one part of the magnetic field generator.

11. A method for performing a magnetic resonance (MR) measurement of an organ structure of a patient using a magnetic resonance imaging (MRI) system configured for imaging of the organ structure, the method comprising:

ascertaining, via a processor, a correct positioning of the organ structure of the patient for the MR measurement;

ascertaining a correct positioning of the MRI system with regard to the positioning of the organ structure of the patient, by acquiring, via the processor: a sensor signal indicative of a correct relative position between the organ structure and at least one reference point of the MRI system, information indicative of a physical characteristic of the patient, and/or localizer image data of the patient;

determining, via the processor, a required modification to the positioning of the MRI system based on the acquired sensor signal, the acquired information, and/or the acquired localizer image data;

automatically adjusting, via the processor, a position of at least one part of a magnetic field generator of the MRI system based on the required modification;

selecting, via the processor, a MR scanning protocol for preforming the MR measurement of the organ structure;

performing a localizer measurement for acquiring localizer image data of the patient, wherein a landmark is detected in the localizer image data, the landmark being a tooth and/or an eye of the patient;

adjusting, via the processor, a spatial coverage of the MR measurement with regard to the organ structure to be imaged based on the landmark in the localizer image data; and controlling, via the processor, the MRI system to perform the MR measurement to acquire MR image data of the organ structure.

12. A method for performing a magnetic resonance (MR) measurement of an organ structure of a patient using a magnetic resonance imaging (MRI) system configured for imaging of the organ structure, the method comprising:

ascertaining, via a processor, a correct positioning of the organ structure of the patient for the MR measurement;

ascertaining a correct positioning of the MRI system with regard to the positioning of the organ structure of the patient, by acquiring, via the processor: a sensor signal indicative of a correct relative position between the organ structure and at least one reference point of the MRI system, information indicative of a physical characteristic of the patient, and/or localizer image data of the patient;

determining, via the processor, a required modification to the positioning of the MRI system based on the acquired sensor signal, the acquired information, and/or the acquired localizer image data;

automatically adjusting, via the processor, a position of at least one part of a magnetic field generator of the MRI system based on the required modification;

selecting, via the processor, a MR scanning protocol for preforming the MR measurement of the organ structure;

performing a localizer measurement for acquiring localizer image data of the patient, the organ structure being segmented in the localizer image data;

adjusting, via the processor, a spatial coverage of the MR measurement with regard to the organ structure to the imaged, wherein:
  the spatial coverage of the MR measurement is automatically adjusted based on a position of the organ structure within the localizer image data in response to the organ structure being completely captured within the localizer image data, and
  a subsequent localizer measurement configured to acquire subsequent localizer image data is performed in response to at least a part of the organ structure is positioned outside of the localizer image data, the spatial coverage of the MR measurement being automatically adjusted based on a position of the organ structure within the subsequent localizer image data; and controlling, via the processor, the MRI system to perform the MR measurement to acquire MR image data of the organ structure.

13. A method for performing a magnetic resonance (MR) measurement of an organ structure of a patient using a magnetic resonance imaging (MRI) system configured for imaging of the organ structure, the method comprising:

ascertaining, via a processor, a correct positioning of the organ structure of the patient for the MR measurement, wherein the organ structure is at least one tooth or at least one eye of the patient, optical image data of the at least one eye and/or a jaw region including the at least one tooth being acquired via an optical sensor;

ascertaining a correct positioning of the MRI system with regard to the positioning of the organ structure of the patient, by acquiring, via the processor: a sensor signal indicative of a current relative position between the organ structure and at least one reference point of the MRI system, information indicative of a physical characteristic of the patient, and/or localizer image data of the patient;

determining, via the processor, a required modification to the positioning of the MRI system based on the acquired sensor signal, the acquired information, and/or the acquired localizer image data;

automatically adjusting, via the processor, a position of at least one part of a magnetic field generator of the MRI system based on the required modification;

selecting, via the processor, a MR scanning protocol for performing the MR measurement of the organ structure;

automatically adjusting, via the processor, a spatial coverage of the MR measurement with regard to the at least one tooth or the at least one eye based on the optical image data; and controlling, via the processor, the MRI system to perform the MR measurement to acquire MR image data of the organ structure.

14. A magnetic resonance imaging (MRI) system, comprising:
  a scanner configured for imaging an organ structure of a patient; and
  a processor configured to:
    ascertain a correct positioning of the organ structure of the patient for a magnetic resonance (MR) measurement;
    ascertain a correct positioning of the scanner with regard to the positioning of the organ structure of the patient, by acquiring a sensor signal indicative of a current relative position between the organ structure and at least one reference point of the scanner; information indicative of a physical characteristic of the patient; and/or localizer image data of the patient, wherein the ascertaining, of the correct positioning of the scanner with regard to the positioning of the organ structure of the patient includes: performing a localizer measurement to acquire the localizer image data of the patient, and detecting a landmark within the localizer image data, the landmark being a tooth and/or an eye of the patient;
    determine a required modification to the positioning of the scanner based on the acquired sensor signal, the acquired information, and/or the acquired localizer image data;
    automatically adjust a position of at least one part of a magnetic field generator of the scanner based on the required modification and the detected landmark;
    select a MR scanning protocol for performing the MR measurement of the organ structure;
    adjust a spatial coverage of the MR measurement with regard to the organ structure to be imaged; and
    control the scanner to perform the MR measurement to acquire MR image data of the organ structure.

15. A method for performing a magnetic resonance (MR) measurement of an organ structure of a patient using a magnetic resonance imaging (MRI) system configured for imaging of the organ structure, the method comprising:

ascertaining, via a processor, a correct positioning of the organ structure of the patient for the MR measurement, the organ structure being at least one tooth or at least one eye of the patient, wherein optical image data of the at least one eye and/or a jaw region includes the at least one tooth being acquired via an optical sensor;

acquiring, via the processor, a sensor signal indicative of a position and/or posture of the patient, the sensor signal being generated by an optical sensor, a distance sensor, a position sensor, a pressure sensor, and/or a thermal sensor;

ascertaining, via the processor, a correct positioning of the MRI system with regard to the positioning of the organ structure of the patient;

selecting, via the processor, a MR scanning protocol for performing the MR measurement of the organ structure;

performing, via the processor, a localizer measurement for acquiring localizer image data of the patient, the organ structure being segmented in the localizer image data;

detecting, via the processor, a landmark in the localizer image data, the landmark being a tooth and/or an eye of the patient;

automatically iteratively adjusting a field of view of the MR measurement, via the processor, based on a body model of the patient and the sensor signal to adjust a spatial coverage of the MR measurement with regard to the organ structure to be imaged, the spatial coverage being automatically adjusted, in response to the organ structure being completely captured within the localizer image data, based the landmark in the localizer image data, a position of the organ structure within the localizer image data, and the optical image data, wherein the spatial coverage of the MR measurement with regard to the organ structure to be imaged is adjusted by automatically modifying a position of the at least one part of the magnetic field generator;

in response to at least a part of the organ structure being positioned outside of the localizer image data, automatically performing, via the processor, a subsequent localizer measurement configured to acquire subsequent localizer image data, the spatial coverage of the MR measurement being automatically adjusted further based on a position of the organ structure within the subsequent localizer image data;

analyzing, via the processor, a position of the patient based on a sensor signal indicative of a current relative position of the organ structure and the MRI system;

providing, via the processor, guidance to the patient with regard to the MR measurement based on the analyzed position of the patient, the providing guidance to the patient including providing visual and/or audible information on at least a posture of the patient; and controlling, via the processor, the MRI system to perform the MR measurement to acquire MR image data of the organ structure.

16. A magnetic resonance imaging (MRI) system, comprising:
a scanner configured for imaging an organ structure of a patient; and
a processor configured to:
ascertain a correct positioning of the organ structure of the patient for a magnetic resonance (MR) measurement, wherein the organ structure is at least one tooth or at least one eye of the patient;
ascertain a correct positioning of the scanner with regard to the positioning of the organ structure of the patient, by acquiring a sensor signal indicative of a current relative position between the organ structure and at least one reference point of the scanner, information indicative of a physical characteristic of the patient, and/or localizer image data of the patient, wherein ascertaining the correct positioning of the scanner includes acquiring optical image data, via an optical sensor, of the at least one eye and/or a jaw region including the at least one tooth;
determine a required modification to the positioning of the scanner based on the acquired sensor signal, the acquired information, and/or the acquired localizer image data;
automatically adjust a position of at least one part of a magnetic field generator of the scanner based on the required modification and the acquired optical image data;
select a MR scanning protocol for performing the MR measurement of the organ structure;
adjust a spatial coverage of the MR measurement with regard to the organ structure to be imaged; and
control the scanner to perform the MR measurement to acquire MR image data of the organ structure.

17. A magnetic resonance imaging (MRI) system, comprising:
a scanner configured for imaging an organ structure of a patient; and
a processor configured to:
ascertain a correct positioning of the organ structure of the patient for a magnetic resonance (MR) measurement;
ascertain a correct positioning of the scanner with regard to the positioning of the organ structure of the patient, by acquiring a sensor signal indicative of a current relative position between the organ structure and at least one reference point of the scanner, information indicative of a physical characteristic of the patient, and/or localizer image data of the patient;
determine a required modification to the positioning of the scanner based on the acquired sensor signal, the acquired information, and/or the acquired localizer image data;
automatically adjust the position of at least one part of a magnetic field generator of the scanner based on the required modification;
select a MR scanning protocol for performing the MR measurement of the organ structure;
acquire a sensor signal indicative of a position of the and/or posture of the patient;
adjust a spatial coverage of the MR measurement with regard to the organ structure to be imaged, wherein the adjusting of the spatial coverage of the MR measurement includes an iterative adjustment of a field of view of the MR measurement based on a body model of the patient and the sensor signal indicative of the position and/or posture of the patient; and
control the scanner to perform the MR measurement to acquire MR image data of the organ structure.

18. A magnetic resonance imaging (MRI) system, comprising:
a scanner configured for imaging an organ structure of a patient; and
a processor configured to:
ascertain a correct positioning of the organ structure of the patient for a magnetic resonance (MR) measurement;
ascertain a correct positioning of the scanner with regard to the positioning of the organ structure of the patient, by acquiring a sensor signal indicative of a current relative position between the organ structure and at least one reference point of the scanner, information indicative of a physical characteristic of the patient, and/or localizer image data of the patient;
determine a required modification to the positioning of the scanner based on the acquired sensor signal, the acquired information, and/or the acquired localizer image data;
automatically adjust a position of at least one part of a magnetic field generator of the scanner based on the required modification;
select a MR scanning protocol for performing the MR measurement of the organ structure;
perform a localizer measurement to acquire localizer image data of the patient, wherein a landmark is detected in the localizer image data, the landmark being a tooth and/or an eye of the patient;
adjust a spatial coverage of the MR measurement with regard to the organ structure to be imaged based on the landmark in the localizer image data; and
control the scanner to perform the MR measurement to acquire MR image data of the organ structure.

19. A magnetic resonance imaging (MRI) system, comprising:
a scanner configured for imaging an organ structure of a patient; and
a processor configured to:

ascertain a correct positioning of the organ structure of the patient for a magnetic resonance (MR) measurement;

ascertain a correct positioning of the scanner with regard to the positioning of the organ structure of the patient, by acquiring a sensor signal indicative of a current relative position between the organ structure and at least one reference point of the scanner, information indicative of a physical characteristic of the patient, and/or localizer image data of the patient;

determine a required modification to the positioning of the scanner based on the acquired sensor signal, the acquired information, and/or the acquired localizer image data;

automatically adjust position of at least one part of a magnetic field generator of the scanner based on the required modification;

select a MR scanning protocol for performing the MR measurement of the organ structure;

perform a localizer measurement to acquire localizer image data of the patient, the organ structure being segmented in the localizer image data;

adjust a spatial coverage of the MR measurement with regard to the organ structure to be imaged, wherein:
the spatial coverage of the MR measurement is automatically adjusted based on a position of the organ structure within the localizer image data in response to the organ structure being completely captured within the localizer image data, and
a subsequent localizer measurement configured to acquire subsequent localizer image data is performed in response to at least a part of the organ structure is positioned outside of the localizer image data, the spatial coverage of the MR measurement being automatically adjusted based on a position of the organ structure within the subsequent localizer image data; and control the scanner to perform the MR measurement to acquire MR image data of the organ structure.

20. A magnetic resonance imaging (MRI) system, comprising:
a scanner configured for imaging an organ structure of a patient; and
a processor configured to:
ascertain a correct positioning of the organ structure of the patient for a magnetic resonance (MR) measurement, the organ structure being at least one tooth or at least one eye of the patient, wherein optical image data of the at least one eye and/or a jaw region including the at least one tooth is acquired via an optical sensor;
ascertain a correct positioning of the scanner with regard to the positioning of the organ structure of the patient, by acquiring a sensor signal indicative of a current relative position between the organ structure and at least one reference point of the MRI system; information indicative of a physical characteristic of the patient; and/or localizer image data of the patient;
determine a required modification to the positioning of the MRI system based on the acquired sensor signal, the acquired information, and/or the acquired localizer image data;
automatically adjust the position of the at least one part of the magnetic field generator based on the required modification;
select a MR scanning protocol for performing the MR measurement of the organ structure;
automatically adjust a spatial coverage of the MR measurement with regard to the organ structure to be imaged based on the optical image data; and
control the scanner to perform the MR measurement to acquire MR image data of the organ structure.

\* \* \* \* \*